United States Patent
Lee et al.

(10) Patent No.: US 10,809,878 B2
(45) Date of Patent: Oct. 20, 2020

(54) METHOD AND APPARATUS FOR DISPLAYING ULTRASOUND IMAGE

(71) Applicant: SAMSUNG MEDISON CO., LTD., Hongcheon-gun (KR)

(72) Inventors: Young-Joo Lee, Seoul (KR); Sung-nam Park, Seongnam-si (KR); Jae-young Eum, Incheon (KR)

(73) Assignee: SAMSUNG MEDISON CO., LTD., Hongcheon-gun (KR)

( * ) Notice: Subject to any disclaimer, the term of this patent is extended or adjusted under 35 U.S.C. 154(b) by 507 days.

(21) Appl. No.: 15/013,313

(22) Filed: Feb. 2, 2016

(65) Prior Publication Data

US 2017/0090694 A1 Mar. 30, 2017

(30) Foreign Application Priority Data

Sep. 25, 2015 (KR) .................. 10-2015-0137089

(51) Int. Cl.
*G06F 3/048* (2013.01)
*G06F 3/0482* (2013.01)
(Continued)

(52) U.S. Cl.
CPC .............. *G06F 3/0482* (2013.01); *A61B 8/08* (2013.01); *A61B 8/463* (2013.01); *A61B 8/465* (2013.01);
(Continued)

(58) Field of Classification Search
CPC .... G06F 19/321; G06F 3/0484; G06F 3/0488; G06F 3/0482; A61B 8/08; A61B 8/463;
(Continued)

(56) References Cited

U.S. PATENT DOCUMENTS

| 7,367,946 B2 | 5/2008 | Kato |
| 8,951,197 B2 | 2/2015 | Matsumura |

(Continued)

FOREIGN PATENT DOCUMENTS

| CN | 1606966 A | 4/2005 |
| CN | 1980606 A | 6/2007 |

(Continued)

OTHER PUBLICATIONS

General Electric Co., Technical Publications Vivid™ E95 / Vivid E90 / Vivid E80 User Manual, , Feb. 26, 2014, Version 202, https://iconnect.aurora.org/ahcweb3/slmcrad/SLMC/Echo/Manuals/GE%20-%20E95%20User%20Manual.pdf.*

(Continued)

*Primary Examiner* — Mohamed Abou El Seoud
(74) *Attorney, Agent, or Firm* — Sughrue Mion, PLLC

(57) ABSTRACT

An ultrasound diagnosis apparatus includes a display configured to display a first cine frame selected by a user from a plurality of cine frames, on a first area on a screen of the ultrasound diagnosis apparatus; a user input unit configured to receive a user input of inputting additional information onto the displayed first cine frame; and a processor configured to generate a reference frame based on the input additional information and the first cine frame and to control the display to display the generated reference frame on a second area on the screen.

20 Claims, 27 Drawing Sheets

(51) Int. Cl.
- *A61B 8/00* (2006.01)
- *A61B 8/08* (2006.01)
- *G06T 7/73* (2017.01)
- *G06F 3/0485* (2013.01)
- *G06F 3/0488* (2013.01)

(52) U.S. Cl.
CPC ............ *A61B 8/468* (2013.01); *G06F 3/0485* (2013.01); *G06T 7/74* (2017.01); *A61B 8/0866* (2013.01); *A61B 8/467* (2013.01); *G06F 3/0488* (2013.01); *G06T 2207/10132* (2013.01)

(58) Field of Classification Search
CPC ......... A61B 8/465; A61B 8/468; A61B 8/461; A61B 8/5215; A61B 8/5223; A61B 8/467; G06T 7/74; G06T 2207/10132
USPC .......................................... 715/771, 700, 838
See application file for complete search history.

(56) References Cited

U.S. PATENT DOCUMENTS

| | | | |
|---|---|---|---|
| 9,223,931 | B2 | 12/2015 | Kim et al. |
| 2005/0090746 | A1 | 4/2005 | Ohtake |
| 2006/0242602 | A1* | 10/2006 | Schechter ........... G06F 3/04817 |
| | | | 715/838 |
| 2007/0143791 | A1* | 6/2007 | Sammarco ........ H04M 1/72522 |
| | | | 725/38 |
| 2008/0193004 | A1 | 8/2008 | Mine |
| 2011/0208052 | A1* | 8/2011 | Entrekin .............. A61B 8/0825 |
| | | | 600/437 |
| 2012/0108960 | A1 | 5/2012 | Halmann et al. |
| 2013/0345563 | A1 | 12/2013 | Stuebe et al. |
| 2014/0221836 | A1 | 8/2014 | Takeda et al. |
| 2015/0164479 | A1 | 6/2015 | Toji |

FOREIGN PATENT DOCUMENTS

| | | |
|---|---|---|
| KR | 0146274 B1 | 5/1998 |
| KR | 10-0740378 B1 | 7/2007 |
| KR | 10-1071015 B1 | 10/2011 |

OTHER PUBLICATIONS

Communication dated Mar. 2, 2017 issued by the European Patent Office in counterpart European Patent Application No. 16153202.3.
Communication dated Jun. 3, 2020, from the National Intellectual Property Administration of P.R. China in Application No. 201610177134.X.

* cited by examiner

METHOD AND APPARATUS FOR DISPLAYING ULTRASOUND IMAGE

CROSS-REFERENCE TO RELATED PATENT APPLICATION

This application claims the benefit of Korean Patent Application No. 10-2015-0137089, filed on Sep. 25, 2015, in the Korean Intellectual Property Office, the disclosure of which is incorporated herein in its entirety by reference.

BACKGROUND

1. Field

The present disclosure relates to a method and apparatus for displaying an ultrasound image to which additional information has been input, in response to a user input of inputting additional information to an ultrasound image.

2. Description of the Related Art

Ultrasound diagnosis apparatuses transmit ultrasound signals generated by transducers of a probe to an object and receive echo signals reflected from the object, thereby obtaining at least one image of an internal part of the object (e.g., soft tissues or blood flow). In particular, ultrasound diagnosis apparatuses are used for medical purposes including observation of the interior of an object, detection of foreign substances, and diagnosis of damage to the object. Such ultrasound diagnosis apparatuses provide high stability, display images in real time, and are safe due to the lack of radioactive exposure, compared to X-ray apparatuses. Therefore, ultrasound diagnosis apparatuses are widely used together with other image diagnosis apparatuses including a computed tomography (CT) apparatus, a magnetic resonance imaging (MRI) apparatus, and the like.

SUMMARY

Provided are apparatuses and methods of providing, as a special image, an ultrasound image to which additional information has been input, in response to a user input of inputting additional information to an ultrasound image.

Provided are also various methods of displaying an ultrasound image to which additional information has been input.

Additional aspects will be set forth in part in the description which follows and, in part, will be apparent from the description, or may be learned by practice of the presented embodiments.

According to an aspect of the present invention, an ultrasound diagnosis apparatus includes a display configured to display a first cine frame selected by a user from a plurality of cine frames, on a first area on a screen of the ultrasound diagnosis apparatus; a user input unit configured to receive a user input of inputting additional information onto the displayed first cine frame; and a processor configured to generate a reference frame based on the input additional information and the first cine frame and to control the display to display the generated reference frame on a second area on the screen.

The user input unit may receive a user input of selecting the reference frame displayed on the second area, and the display may display the selected reference frame on the first area.

The user input unit may receive a user input of selecting a second cine frame from the plurality of cine frames by scrolling the plurality of cine frames in an order of being captured, and a user input of selecting the reference frame displayed on the second area. In response to the user input of selecting the reference frame displayed on the second area, the processor may change the selected cine frame from the second cine frame to the first cine frame corresponding to the selected reference frame.

The display may display a marker representing a capturing order of the selected cine frame, and, as the first cine frame is determined as a cine frame selected via scrolling, the display may change the displayed marker to a marker representing that the selected cine frame has changed from the second cine frame to the first cine frame, and display the changed marker representing that the selected cine frame has changed from the second cine frame to the first cine frame.

A plurality of reference frames including the generated reference frame may be displayed on the second area, the processor may receive a user input of rotating a knob included in the ultrasound diagnosis apparatus, and, in response to the user input of rotating the knob, the processor may control the display so that the plurality of reference frames are sequentially selected.

A plurality of reference frames including the generated reference frame may be displayed on the second area, the display may display a user interface (UI) for selecting a type of the additional information, the user input unit may receive a user input of selecting one from various types of the additional information, via the UI, and the processor may control the display to preferentially display, on the second area, a reference frame to which additional information of the selected type has been input from among the plurality of reference frames.

A plurality of reference frames including the generated reference frame may be displayed on the second area, and, in response to a user input of selecting the first cine frame, the processor may control the display to preferentially display a reference frame captured at a time point close to the time point when the selected first cine frame is captured, from among the plurality of reference frames.

The user input unit may receive a user input of re-selecting the first cine frame from the plurality of cine frames by scrolling the plurality of cine frames in an order of being captured. As the first cine frame is re-selected, the processor may control the display to display, on the reference frame displayed on the second area, a marker representing that the reference frame displayed on the second area is a reference frame corresponding to the first cine frame.

A plurality of reference frames including the generated reference frame may be displayed on the second area. In response to a user input of inputting additional information onto the first cine frame, the processor may control the display to preferentially display a reference frame to which a same type of additional information as a type of the input additional information has been input, from among the plurality of reference frames.

A plurality of reference frames including the generated reference frame may be displayed on the second area, the user input unit may receive a user input of selecting at least one reference frame from the plurality of reference frames, and the processor may control the display to display the at least one reference frame as a group.

According to an aspect of the present invention, a method of displaying an ultrasound image includes displaying a first cine frame selected by a user from a plurality of cine frames, on a first area on a screen of an ultrasound diagnosis apparatus; receiving a user input of inputting additional information onto the displayed first cine frame; generating a reference frame based on the input additional information and the first cine frame; and displaying the generated reference frame on a second area on the screen.

The method may further include receiving a user input of selecting the reference frame displayed on the second area; and displaying the selected reference frame on the first area.

The method may further include receiving a user input of selecting a second cine frame from the plurality of cine frames by scrolling the plurality of cine frames in an order of being captured; receiving a user input of selecting the reference frame displayed on the second area; and, in response to the user input of selecting the reference frame displayed on the second area, changing the selected cine frame from the second cine frame to the first cine frame corresponding to the selected reference frame.

The method may further include displaying a marker representing a capturing order of the selected cine frame; and changing the displayed marker to a marker representing that the selected cine frame has changed from the second cine frame to the first cine frame.

A plurality of reference frames including the generated reference frame may be displayed on the second area, and the method may further include receiving a user input of rotating a knob included in the ultrasound diagnosis apparatus; and, in response to the user input of rotating the knob, sequentially selecting the plurality of reference frames.

A plurality of reference frames including the generated reference frame may be displayed on the second area, and the method may further include displaying a user interface (UI) for selecting a type of the additional information; receiving a user input of selecting one from various types of the additional information, via the UI; and preferentially displaying, on the second area, a reference frame to which additional information of the selected type has been input from among the plurality of reference frames.

A plurality of reference frames including the generated reference frame may be displayed on the second area, and the method may further include, in response to a user input of selecting the first cine frame, preferentially displaying a reference frame captured at a time point close to the time point when the selected first cine frame is captured, from among the plurality of reference frames.

The method may further include receiving a user input of re-selecting the first cine frame from the plurality of cine frames by scrolling the plurality of cine frames in an order of being captured; and, as the first cine frame is re-selected, displaying, on the reference frame displayed on the second area, a marker representing that the reference frame displayed on the second area is a reference frame corresponding to the first cine frame.

A plurality of reference frames including the generated reference frame may be displayed on the second area, and the method may further include, in response to a user input of inputting additional information onto the first cine frame, preferentially displaying a reference frame to which a same type of additional information as a type of the input additional information has been input, from among the plurality of reference frames.

A plurality of reference frames including the generated reference frame may be displayed on the second area, and the method may further include receiving a user input of selecting at least one reference frame from the plurality of reference frames; and displaying the at least one reference frame as a group.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1:
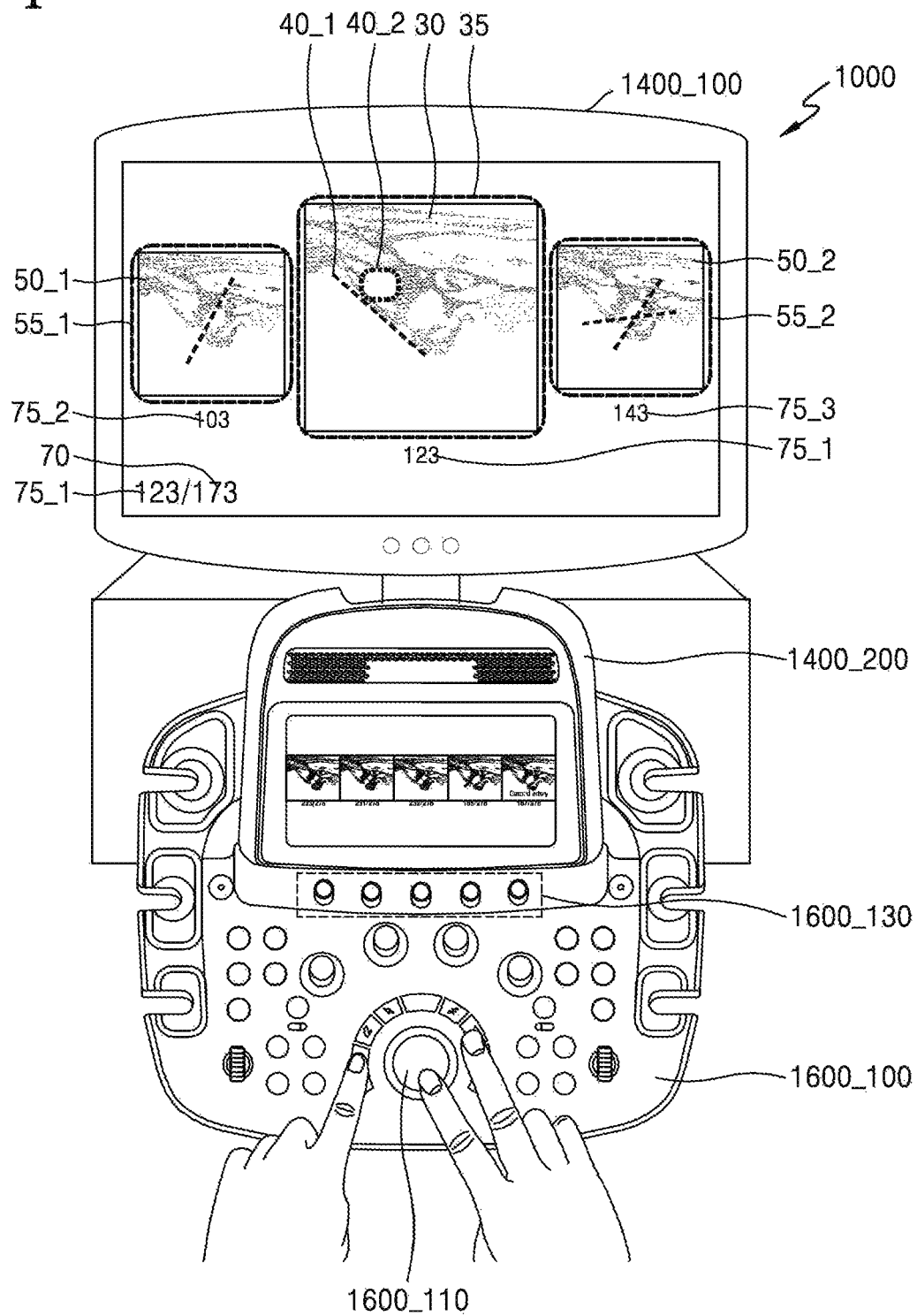
FIG. 1 illustrates an exemplary embodiment in which an ultrasound diagnosis apparatus generates a reference frame.

The terms used in this specification are those general terms currently widely used in the art in consideration of functions regarding the inventive concept, but the terms may vary according to the intention of those of ordinary skill in the art, precedents, or new technology in the art. Also, some terms may be arbitrarily selected by the applicant, and in this case, the meaning of the selected terms will be described in detail in the detailed description of the present specification. Thus, the terms used herein have to be defined based on the meaning of the terms together with the description throughout the specification.

When a part "includes" or "comprises" an element, unless there is a particular description contrary thereto, the part can further include other elements, not excluding the other elements. In addition, terms such as " . . . unit", " . . . module", or the like refer to units that perform at least one function or operation, and the units may be implemented as hardware or software or as a combination of hardware and software.

Reference will now be made in detail to embodiments, examples of which are illustrated in the accompanying drawings. In this regard, the present embodiments may have different forms and should not be construed as being limited to the descriptions set forth herein. In the drawings, parts irrelevant to the description are omitted for simplicity of explanation, and like numbers refer to like elements throughout.

Throughout the specification, an "ultrasound image" refers to an image of an object, which is obtained using ultrasound waves. Furthermore, an "object" may be a human, an animal, or a part of a human or animal. For example, the object may be an organ (e.g., the liver, the heart, the womb, the brain, a breast, or the abdomen), a blood vessel, or a combination thereof. Also, the object may be a phantom. The phantom means a material having a density, an effective atomic number, and a volume that are approximately the same as those of an organism. For example, the phantom may be a spherical phantom having properties similar to a human body.

Throughout the specification, a "user" may be, but is not limited to, a medical expert, for example, a medical doctor, a nurse, a medical laboratory technologist, or a medical imaging expert, or a technician who repairs medical apparatuses.

Throughout the specification, the term "additional information" may denote detailed information about a target within an ultrasound image. For example, the additional information may include a figure set on the ultrasound image to measure the target or a result of the measurement. The additional information may include a comment input onto the ultrasound image. The comment may include, but is not limited to, a body marker, an arrow, or a text comment.

Embodiments now will be described more fully hereinafter with reference to the accompanying drawings.

FIG. 1 illustrates an exemplary embodiment in which an ultrasound diagnosis apparatus 1000 generates a reference frame.

Referring to FIG. 1, the ultrasound diagnosis apparatus 1000 may generate, as a reference frame, a cine frame to which additional information has been input, in response to a user input of inputting additional information to a cine frame, and display the generated reference frame.

The cine frame is an ultrasound image generated by the ultrasound diagnosis apparatus 1000 imaging a target. The cine image may be an ultrasound image that is not permanently stored in the ultrasound diagnosis apparatus 1000 by a user. For example, as imaging of the target is performed for a certain period of time, the ultrasound diagnosis apparatus 1000 may acquire a plurality of ultrasound images respectively representing the target at a plurality of time points included in the certain period of time, and arrange the plurality of ultrasound images in chronological order.

As a cine frame is generated, the ultrasound diagnosis apparatus 1000 may store the generated cine frame in a buffer set on a volatile memory. The buffer in which the cine frame is stored may be referred to as a cine buffer in some cases, and may be implemented in a ring shape.

Unless the ultrasound diagnosis apparatus 1000 receives a user input of storing a cine frame stored in a buffer in a non-volatile memory, the ultrasound diagnosis apparatus 1000 may not store the cine frame in the non-volatile memory. Accordingly, when the cine buffer runs short of capacity to store a new cine frame, the ultrasound diagnosis apparatus 1000 may delete an already stored cine frame and store the new cine frame. When the ultrasound diagnosis apparatus 1000 is turned off, all of the cine frames stored in the cine buffer may be deleted because of the characteristics of the volatile memory.

The ultrasound diagnosis apparatus 1000 may display a generated cine frame 30 on a first area 35 of a screen of the ultrasound diagnosis apparatus 1000. In this case, the ultrasound diagnosis apparatus 1000 may display the number 70 of generated cine frames and an order number 75_1 of the cine frame 30 indicating the order in which the cine frame 30 is displayed on the screen. For example, as shown in FIG. 1, the screen may show that the displayed cine frame 30 is a 123th cine frame from among a total number of 173 cine frames.

The ultrasound diagnosis apparatus 1000 may sequentially display the cine frames in a capturing order or in a direction opposite to the capturing order. For example, the ultrasound diagnosis apparatus 1000 may receive a user input of selecting one from a plurality of cine frames by scrolling the plurality of cine frames in the capturing order or in the direction opposite to the capturing order. For example, as shown in FIG. 1, in response to a user input of turning a track ball 1600_110 within a control panel 1600_100 right, the ultrasound diagnosis apparatus 1000 may display a frame next to a currently displayed cine frame on the first area 35. In response to a user input of turning the track ball 1600_110 left, the ultrasound diagnosis apparatus 1000 may display a frame previous to the currently displayed cine frame on the first area 35.

The ultrasound diagnosis apparatus 1000 may receive a user input of displaying additional information on a cine frame. The additional information may denote detailed information about a target within the cine frame. For example, the additional information may include a figure set on the cine frame to measure the target or a result of the measurement. The additional information may include a comment input onto the cine frame. The comment may include, but is not limited to, a body marker, an arrow, or a text comment.

As shown in FIG. 1, in response to a user input of measuring a distance between two points within the cine frame 30, the ultrasound diagnosis apparatus 1000 may display a straight line 40_1 linking two points with each other on the cine frame 30. In response to a user input of measuring a width of an oval region within the cine frame 30, the ultrasound diagnosis apparatus 1000 may display an oval 40_2 representing a measured region on the cine frame 30.

In response to a user input of inputting additional information to a cine frame, the ultrasound diagnosis apparatus 1000 may generate, as a reference frame, a cine frame to which additional information has been input. In this case, even when the ultrasound diagnosis apparatus 1000 does not receive a user input of storing a cine frame to which additional information has been input, the ultrasound diagnosis apparatus 1000 may automatically generate the cine frame to which the additional information has been input, as the reference frame.

For example, in response to a user input of measuring a distance between two points within the cine frame 30, the ultrasound diagnosis apparatus 1000 may generate, as the reference frame, the cine frame 30 on which the straight line 40_1 linking the two points with each other is displayed, even when no user inputs of generating the reference frame are received.

The ultrasound diagnosis apparatus 1000 may generate a plurality of reference frames, based on a single cine frame. For example, when the target is a fetus, in response to a user input of measuring a crown-rump length (CRL) of the fetus within the cine frame, the ultrasound diagnosis apparatus 1000 may generate a first reference frame including additional information representing the measured CLR, calculate a Gestational age based on the measured CLR, and generate a second reference frame including additional information representing the calculated Gestational age. The ultrasound diagnosis apparatus 1000 may generate a third reference frame representing both the CLR and the Gestational age.

The ultrasound diagnosis apparatus 1000 may select some from the plurality of cine frames and generate reference frames respectively associated with the selected cine frames. For example, the ultrasound diagnosis apparatus 1000 may select first and second cine frames from the plurality of cine frames. The ultrasound diagnosis apparatus 1000 may generate a first reference frame associated with the first cine frame and a second reference frame associated with the second cine frame.

The ultrasound diagnosis apparatus 1000 may store the generated reference frames. The ultrasound diagnosis apparatus 1000 may store the generated reference frames in a buffer set in volatile memory or in a separate storage set in non-volatile memory.

Accordingly, even when a user does not perform a special operation of storing a frame measured by the user or commented on by the user, the user may store a cine frame measured or commented on by the user.

The ultrasound diagnosis apparatus 1000 may display reference frames 50_1 and 50_2 on second areas 55_1 and 55_2 of the screen. Even when the ultrasound diagnosis apparatus 1000 does not receive a user input of displaying a reference frame, the ultrasound diagnosis apparatus 1000 may automatically display generated reference frames.

The ultrasound diagnosis apparatus 1000 may display order numbers 75_2 and 75_3 indicating orders in which the reference frames 50_1 and 50_2 were captured, together with the reference frames 50_1 and 50_2.

In some cases, the screen of the ultrasound diagnosis apparatus 1000 may include a main screen and a sub-screen. The main screen may be the screen of a main display 1400_100, and the sub-screen may be the screen of a sub-display 1400_200. In this case, the ultrasound diagnosis apparatus 1000 may display the cine frame 30 on the screen of the main display 1400_100 and display the reference frames 50_1 and 50_2 on the screen of the sub-display 1400_200.

In response to a user input of selecting a reference frame, the ultrasound diagnosis apparatus 1000 may display a selected reference frame on the first area 35, on which the cine frame 30 is displayed. In some cases, in response to the user input of selecting a reference frame, the ultrasound diagnosis apparatus 1000 may display a cine frame corresponding to a selected reference frame on the first area 35.

In response to the user input of selecting a reference frame, the ultrasound diagnosis apparatus 1000 may determine a cine frame corresponding to the selected reference frame from among the plurality of cine frames, as a cine frame selected via scrolling. Thus, even when a user does not perform scrolling, the user may move to the cine frame corresponding to the selected reference frame.

Figure 2:
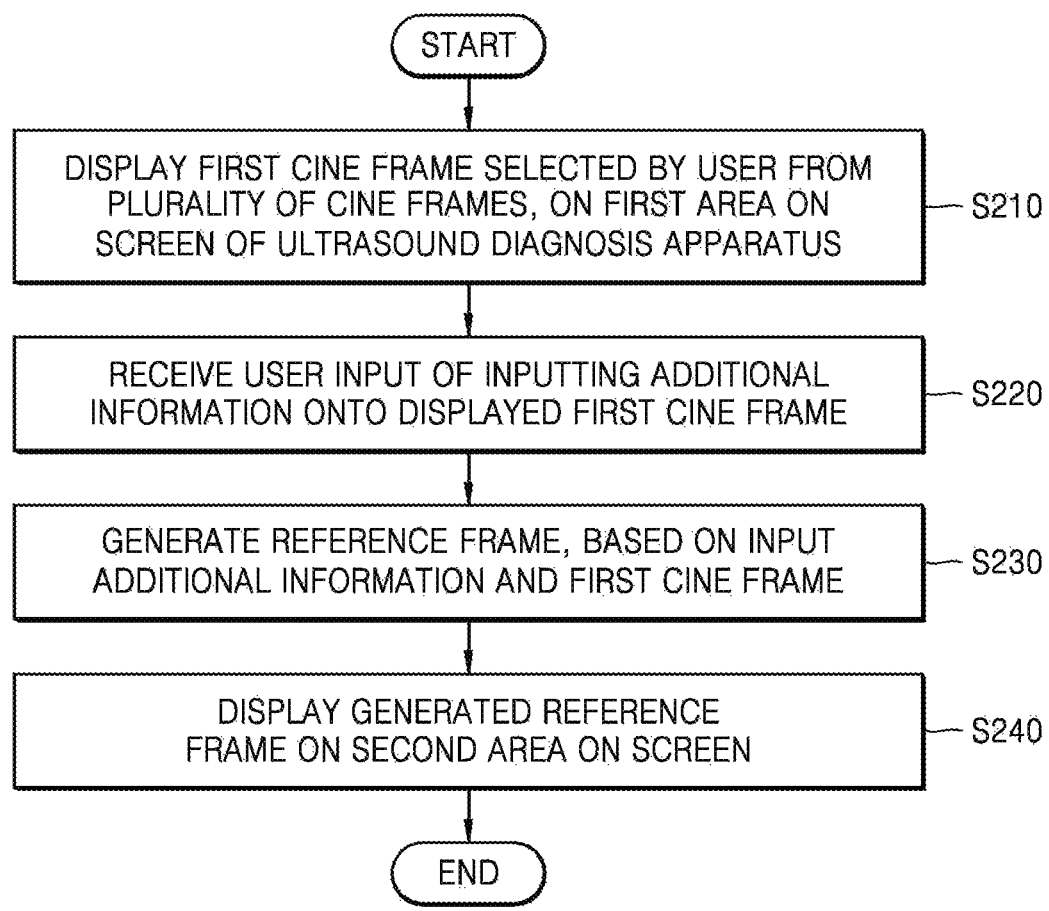
FIG. 2 is a flowchart of an exemplary embodiment in which the ultrasound diagnosis apparatus displays a reference frame.

FIG. 2 is a flowchart of an exemplary embodiment in which the ultrasound diagnosis apparatus 1000 displays a reference frame.

In operation S210, the ultrasound diagnosis apparatus 1000 may display a first cine frame selected by a user from a plurality of cine frames, on a first area on the screen of the ultrasound diagnosis apparatus 1000.

The ultrasound diagnosis apparatus 1000 may receive a user input of selecting the first cine frame from the plurality of cine frames by scrolling the plurality of cine frames in a capturing order or in a direction opposite to the capturing order. For example, the user input of selecting the first cine frame from the plurality of cine frames may include, but is not limited to, a user input of moving a track ball within a control panel, a user input of dragging a scroll bar displayed on the screen, or a user input of swiping the plurality of cine frames.

In operation S220, the ultrasound diagnosis apparatus 1000 may receive a user input of inputting additional information onto the displayed first cine frame.

The additional information may denote detailed information about the target within the cine frame. For example, the additional information may include an object set on the cine frame to measure the target. For example, the object may include a marker displayed on two points within the cine frame to measure a distance between the two points. The object may include a straight line that links two points and that is displayed on the cine frame to measure the distance between the two points. The object may include an oval displayed on the cine frame to measure a width of an oval region, a girth thereof, or a ratio between a major axis and a minor axis of the oval region. The object may also include a looped curve displayed on the cine frame to measure a width of a looped curve region and a length thereof. The object may also include two intersecting straight lines that are displayed on the cine frame to measure an angle between the two straight lines. The object may also include a disk volume displayed on the cine frame to measure the volume of a heart. An object displayed on the cine frame to measure the target within the cine frame may include, but is not limited to, a dot, a line, a figure, or a three-dimensional (3D) figure.

The additional information may include a measurement value of the target within the cine frame. The measurement value of the target may include, but is not limited to, a distance, a width, a length, a volume, a ratio, or an angle.

The additional information may include a comment on the target within the cine frame. For example, the ultrasound diagnosis apparatus 1000 may receive a user input of inputting a comment on the target within the cine frame. The comment on the target may include, but is not limited to, a text, an arrow, a body marker, or a figure. The ultrasound diagnosis apparatus 1000 may receive a user input of inputting, as a comment, a text directly input by a user typing a keyboard provided by the ultrasound diagnosis apparatus 1000. The ultrasound diagnosis apparatus 1000 may receive a user input of inputting a preset word to the ultrasound diagnosis apparatus 1000.

In operation S230, the ultrasound diagnosis apparatus 1000 may generate, as a reference frame, the first cine frame including the additional information, in response to a user input of inputting additional information.

In response to the user input of receiving additional information, the ultrasound diagnosis apparatus 1000 may generate the first cine frame including the additional information as the reference frame, even when a special user input of generating the first cine frame including the additional information as the reference frame is not received.

For example, the ultrasound diagnosis apparatus 1000 may generate the first cine frame including the additional information as the reference frame, in response to a user input of inputting the additional information to the first cine frame and moving to another cine frame.

For example, in response to a user input of selecting a button for inputting the additional information to the first cine frame, the ultrasound diagnosis apparatus 1000 may determine the first cine frame as a cine frame that is to be generated as the reference frame. Then, in response to a user input of moving to another cine frame, the ultrasound diagnosis apparatus 1000 may generate the determined first cine frame as the reference frame. In this case, for a reason such as the user's cancellation of selection of the button for inputting the additional information, even when the additional information is not input onto the first cine frame at the moment when the user input of moving to another cine frame is received, the ultrasound diagnosis apparatus 1000 may generate the first cine frame as the reference frame.

For example, the ultrasound diagnosis apparatus 1000 may generate the first cine frame including the additional information as the reference frame, every time a comment is input onto the first cine frame or a measurement is completed.

In operation S240, the ultrasound diagnosis apparatus 1000 may display the generated reference frame on a second area on the screen.

The ultrasound diagnosis apparatus 1000 may display the generated reference frame on a second area that is different from the first area on the screen. The first area and the second area may be different areas included in a single screen. When the ultrasound diagnosis apparatus 1000 includes a plurality of screens, the first area and the second area may be areas respectively included in different screens.

Even when there are no user inputs of displaying a reference frame, the ultrasound diagnosis apparatus 1000 may display the generated reference frame in response to the user input of inputting the additional information.

The ultrasound diagnosis apparatus 1000 may store the generated reference frame. In some cases, the ultrasound diagnosis apparatus 1000 may store the generated reference frame in a space where the first cine frame is stored. Accordingly, the first cine frame may be replaced with the reference frame. In some cases, the ultrasound diagnosis apparatus 1000 may store the reference frame in a separate buffer set on a volatile memory other than a cine buffer. In this case, the ultrasound diagnosis apparatus 1000 may store a capturing order or ID information of the first cine frame in correspondence with the reference frame. In some cases, the ultrasound diagnosis apparatus 1000 may store the reference frame in a separate space set on a non-volatile memory.

The ultrasound diagnosis apparatus 1000 may store only the additional information. In this case, the ultrasound diagnosis apparatus 1000 may store the capturing order or ID information of the first cine frame in correspondence with the additional information. The ultrasound diagnosis apparatus 1000 may store information about a location on the first cine frame on which the additional information is displayed, in correspondence with the additional information.

In response to a user input of selecting a reference frame, the ultrasound diagnosis apparatus 1000 may display a selected reference frame on the first area.

When a second cine frame has been selected from the plurality of cine frames by scrolling, the ultrasound diagnosis apparatus 1000 may change a selected cine frame from the second cine frame to the first cine frame, which corresponds to the selected reference frame, in response to a user input of selecting a reference frame.

The ultrasound diagnosis apparatus 1000 may display a marker representing a capturing order of the selected cine frame. The marker representing the capturing order of the selected cine frame may be the overall number of cine frames and a numeral representing the capturing order of the selected cine frame. The marker representing the capturing order of the selected cine frame may be a scroll bar in which the plurality of cine frames are mapped according to the capturing order, but is not limited thereto.

As the first cine frame is determined as the cine frame selected via scrolling, the ultrasound diagnosis apparatus 1000 may change the displayed marker to a marker representing that the selected cine frame has changed from the second cine frame to the first cine frame.

When the plurality of reference frames have been displayed on the second area, the ultrasound diagnosis apparatus 1000 may sequentially select the plurality of reference frames in response to a user input of rotating a knob included in the ultrasound diagnosis apparatus 1000.

When the plurality of reference frames have been displayed on the second area, the ultrasound diagnosis apparatus 1000 may receive a user input of selecting one from various types of additional information, via a user interface (UI). In response to the user input of selecting one from various types of additional information, the ultrasound diagnosis apparatus 1000 may preferentially display, on the second area, a reference frame to which the selected type has been input from among the plurality of reference frames.

When the plurality of reference frames have been displayed on the second area and the ultrasound diagnosis apparatus 1000 receives a user input of selecting the first cine frame, the ultrasound diagnosis apparatus 1000 may preferentially display a reference frame captured at a time point close to the time point when the selected first cine frame is captured, from among the plurality of reference frames.

In response to the user input of selecting the first cine frame, the ultrasound diagnosis apparatus 1000 may display a marker representing a reference frame corresponding to the selected first cine frame, on the reference frame corresponding to the selected first cine frame.

When the plurality of reference frames have been displayed on the second area and the ultrasound diagnosis apparatus 1000 receives a user input of inputting the additional information onto the first cine frame, the ultrasound diagnosis apparatus 1000 may preferentially display, on the second area, a reference frame to which the same type of additional information as that of the input additional information has been input, from among the plurality of reference frames.

When the plurality of reference frames have been displayed on the second area, the ultrasound diagnosis apparatus 1000 may display at least one reference frame as a group, in response to a user input of selecting at least one reference frame from the plurality of reference frames.

Figure 3A:
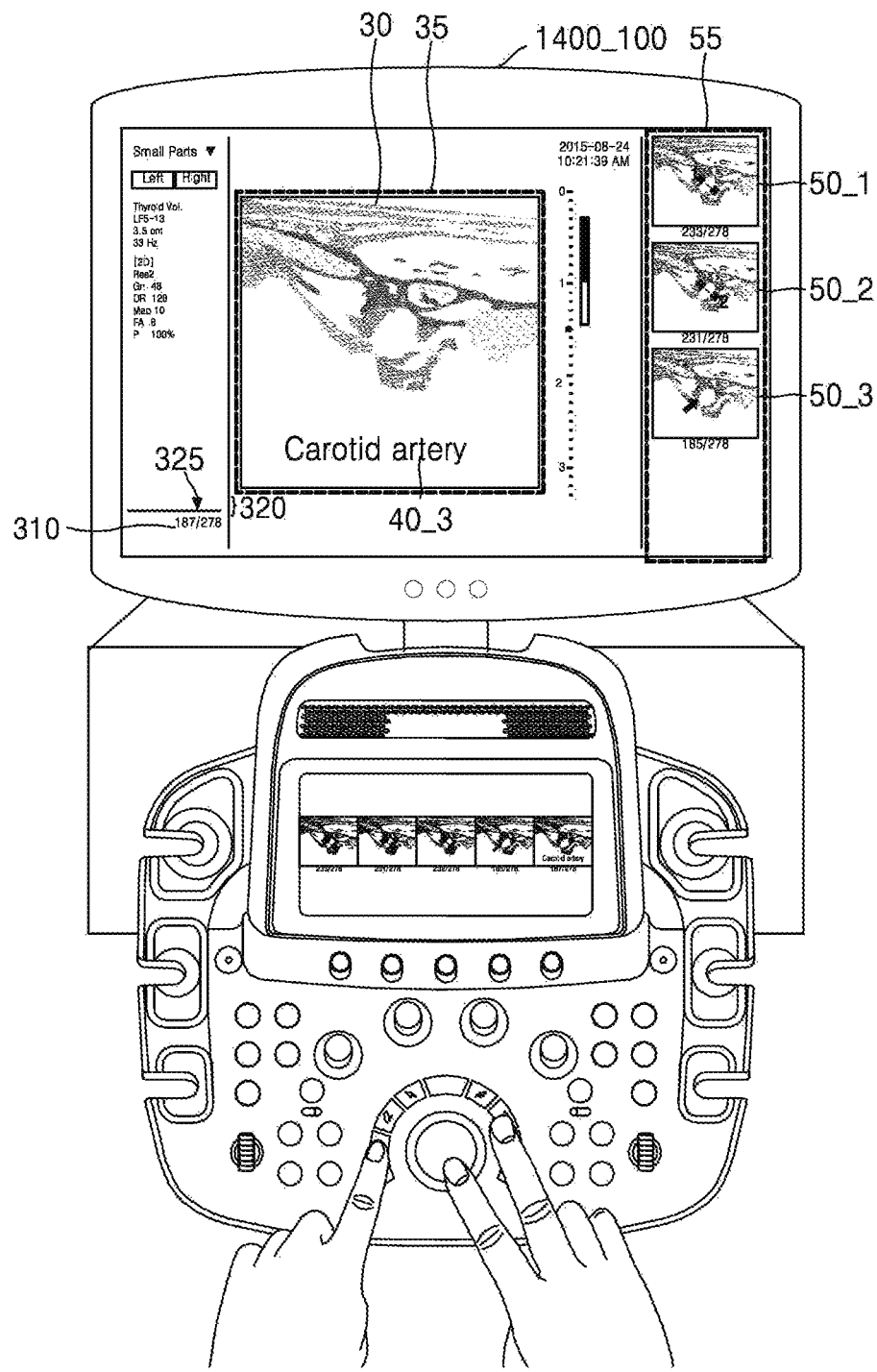
FIGS. 3A and 3B illustrate an exemplary embodiment in which the ultrasound diagnosis apparatus displays a reference frame.
Figure 3B:
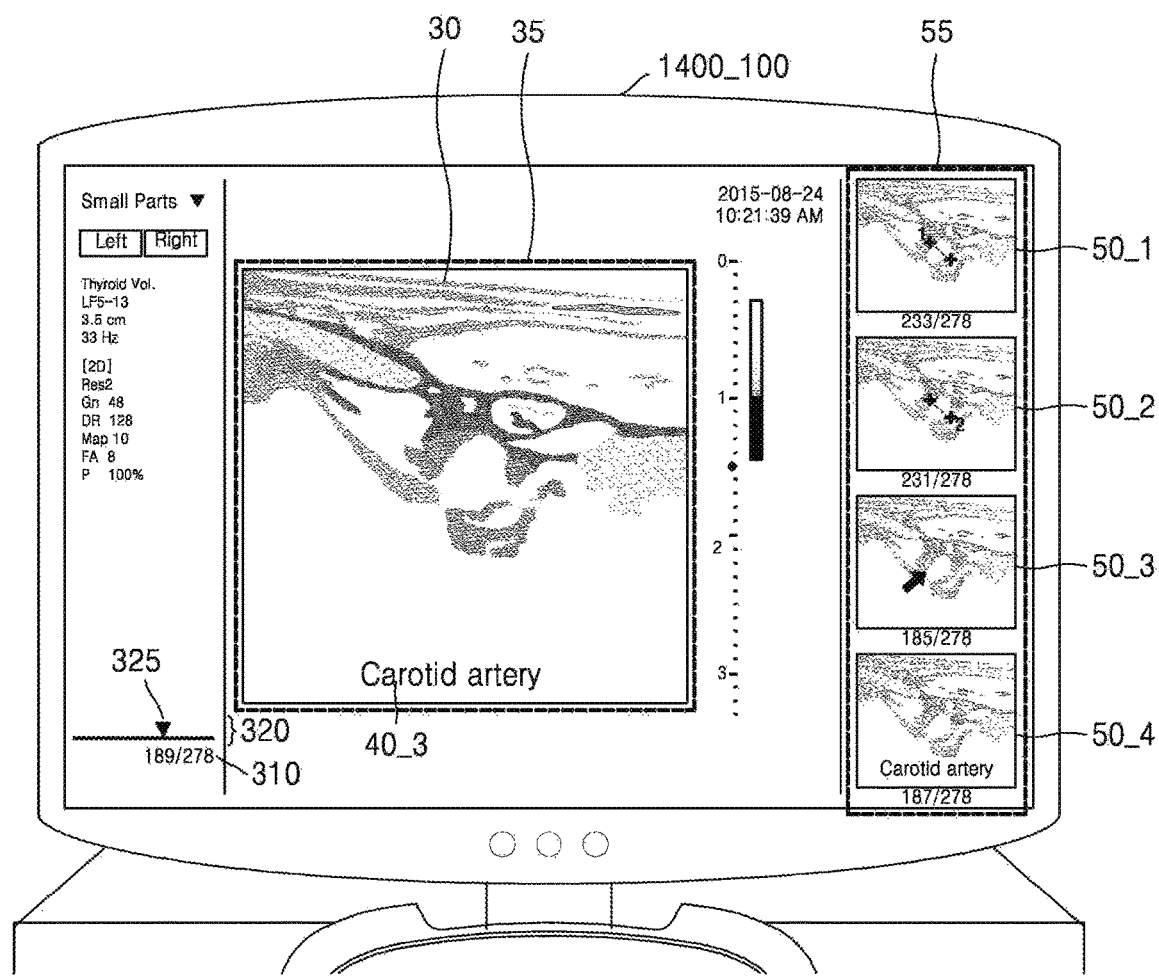

FIGS. 3A and 3B illustrate an exemplary embodiment in which the ultrasound diagnosis apparatus 1000 displays a reference frame.

Referring to FIG. 3A, the ultrasound diagnosis apparatus 1000 may receive a user input of inputting additional information 40_3 onto the cine frame 30.

In response to a user input of scrolling a plurality of cine frames, the ultrasound diagnosis apparatus 1000 may display the cine frame 30 selected from the plurality of cine frames, on the first area 35 of the screen.

In response to the user input of scrolling a plurality of cine frames, the ultrasound diagnosis apparatus 1000 may change a marker (e.g., 310 or 320) representing a capturing order of the selected cine frame. The marker representing the capturing order of the selected cine frame may be a marker 310 representing, as a numeral, the capturing order of the cine frame selected from the plurality of cine frames, or may be a scroll bar 320 representing the capturing order of the selected cine frame as a location on a bar.

In response to the user input of scrolling the plurality of cine frames, the ultrasound diagnosis apparatus 1000 may change the numeral 310 indicating the selected cine frame. In response to the user input of scrolling a plurality of cine frames, the ultrasound diagnosis apparatus 1000 may change the location of a marker 325 representing a capturing order of the selected cine frame, on the scroll bar 320.

The ultrasound diagnosis apparatus 1000 may display a plurality of reference frames 50_1, 50_2, and 50_3 on a second area 55 of the screen.

Referring to FIG. 3B, in response to a user input of inputting a text 40_3 as a comment onto the displayed cine frame 30, the ultrasound diagnosis apparatus 1000 may generate the cine frame 30 including the input text 40_3 as a reference frame 50_4 and display the reference frame 50_4 on the second area 55, even when there are no user inputs of generating or displaying the reference frame 50_4.

For example, the ultrasound diagnosis apparatus 1000 may generate the cine frame 30 including the text 40-3 as the reference frame 50_4, in response to a user input of inputting the text 40-3 onto the cine frame 30 and moving to another cine frame.

For example, the ultrasound diagnosis apparatus 1000 may determine the cine frame 30 as a cine frame that is to be generated as the reference frame 50_4, in response to a user input of selecting a button for inputting the text 40-3 onto the cine frame 30.

For example, as inputting of the text 40-3 as a single text onto the cine frame 30 is completed, the ultrasound diagnosis apparatus 1000 may generate the cine frame 30 including the text 40-3, as the reference frame 50_4.

As the reference frame 50_4 is generated, the ultrasound diagnosis apparatus 1000 may display the generated reference frame 50_4 on the second area 55.

Figure 4:
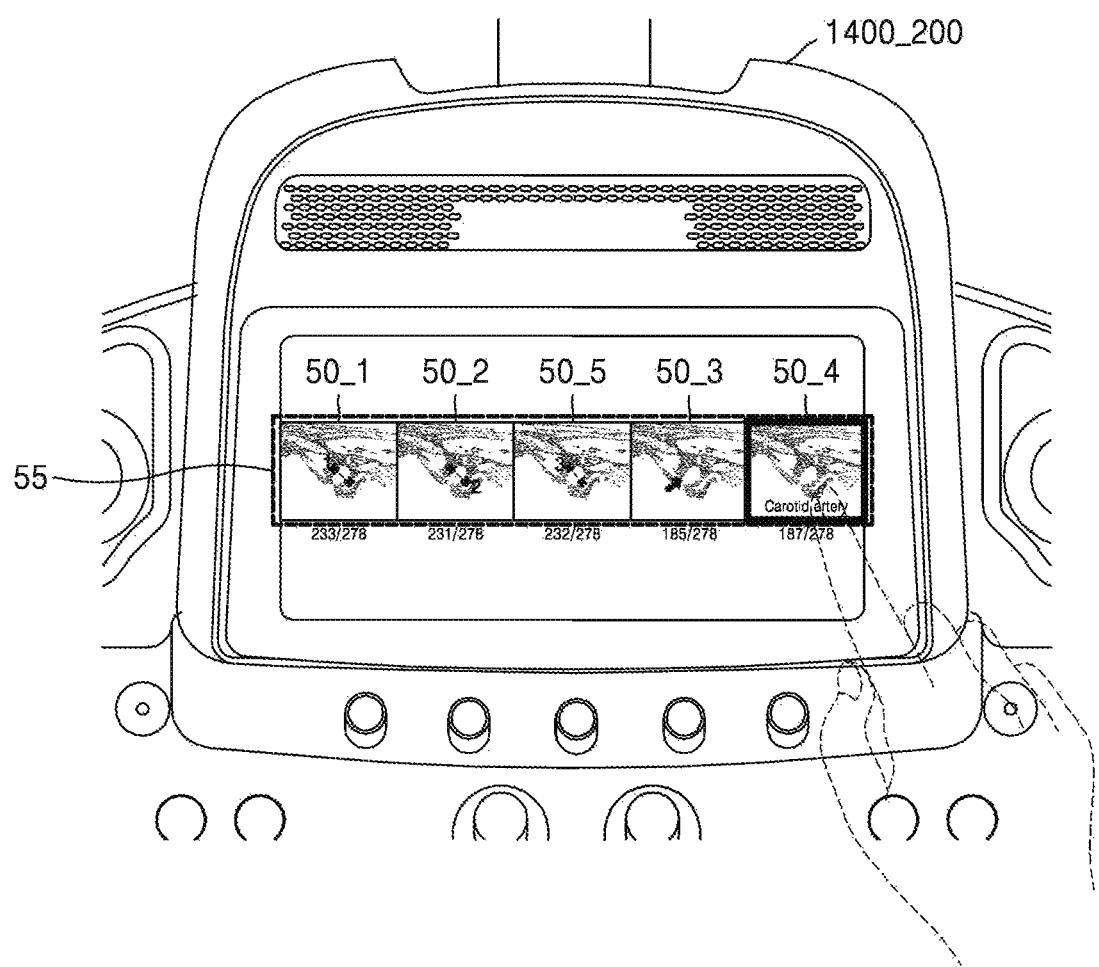
FIG. 4 illustrates an exemplary embodiment in which the ultrasound diagnosis apparatus displays a reference frame on a sub-screen.

FIG. 4 illustrates an exemplary embodiment in which the ultrasound diagnosis apparatus 1000 displays a reference frame on a sub-screen.

Referring to FIG. 4, the ultrasound diagnosis apparatus 1000 may display reference frames 50_1 through 50_5 on a separate screen other than a screen on which the cine frame 30 is displayed.

The ultrasound diagnosis apparatus 1000 may include a main screen and a sub-screen. The sub-screen may be the screen of the sub-display 1400_200, and may be implemented as a touch display. The sub-display 1400_200 may be disposed between the main display 1400_100 and the control panel 1600_100. The ultrasound diagnosis apparatus 1000 may display a UI object on the sub-screen and may receive a user input of touching the UI object.

In response to a user input of inputting additional information to the cine frame displayed on the main screen, the ultrasound diagnosis apparatus 1000 may generate, as a reference frame, a cine frame including the input additional information, and display the generated reference frame on a second area 55 of the sub-screen.

The ultrasound diagnosis apparatus 1000 may receive a touch input of selecting one from the reference frames 50_1 through 50_5 on the sub-screen. The ultrasound diagnosis apparatus 1000 may display the selected reference frame on the main screen.

Figure 5:
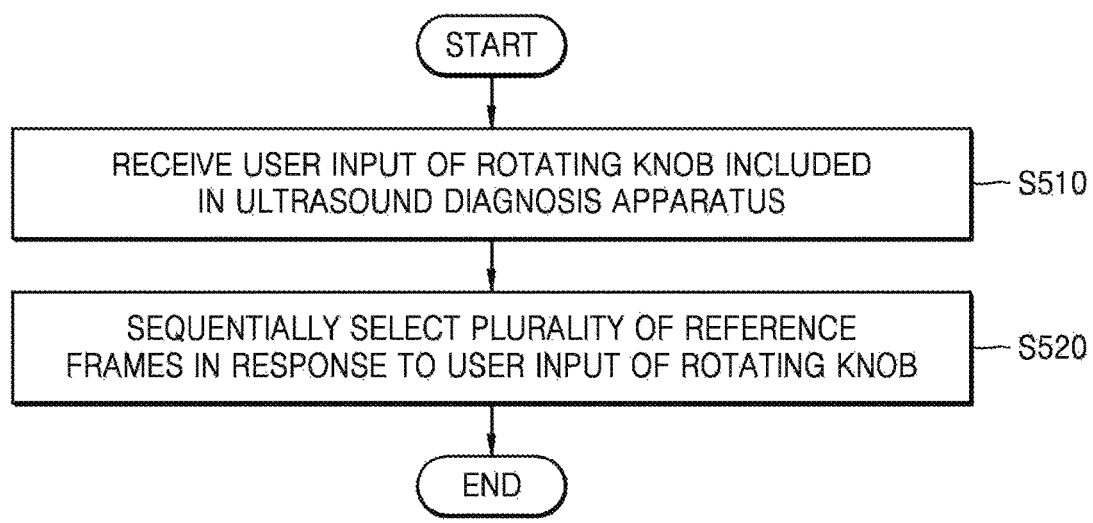
FIG. 5 is a flowchart of an exemplary embodiment in which the ultrasound diagnosis apparatus receives a user input of selecting a reference frame.

FIG. 5 is a flowchart of an exemplary embodiment in which the ultrasound diagnosis apparatus 1000 receives a user input of selecting a reference frame.

In operation S510, the ultrasound diagnosis apparatus 1000 may receive a user input of rotating a knob included in the ultrasound diagnosis apparatus 1000.

The ultrasound diagnosis apparatus 1000 may include the knob in a control panel of the ultrasound diagnosis apparatus 1000. The knob may be a physical button that rotates at a certain angle.

In operation S520, the ultrasound diagnosis apparatus 1000 may sequentially select a plurality of reference frames in response to the user input of rotating the knob.

Even when the ultrasound diagnosis apparatus 1000 does not receive a special user input of selecting a reference frame, the ultrasound diagnosis apparatus 1000 may automatically sequentially select the plurality of reference frames in response to the user input of rotating the knob.

Figure 6A:
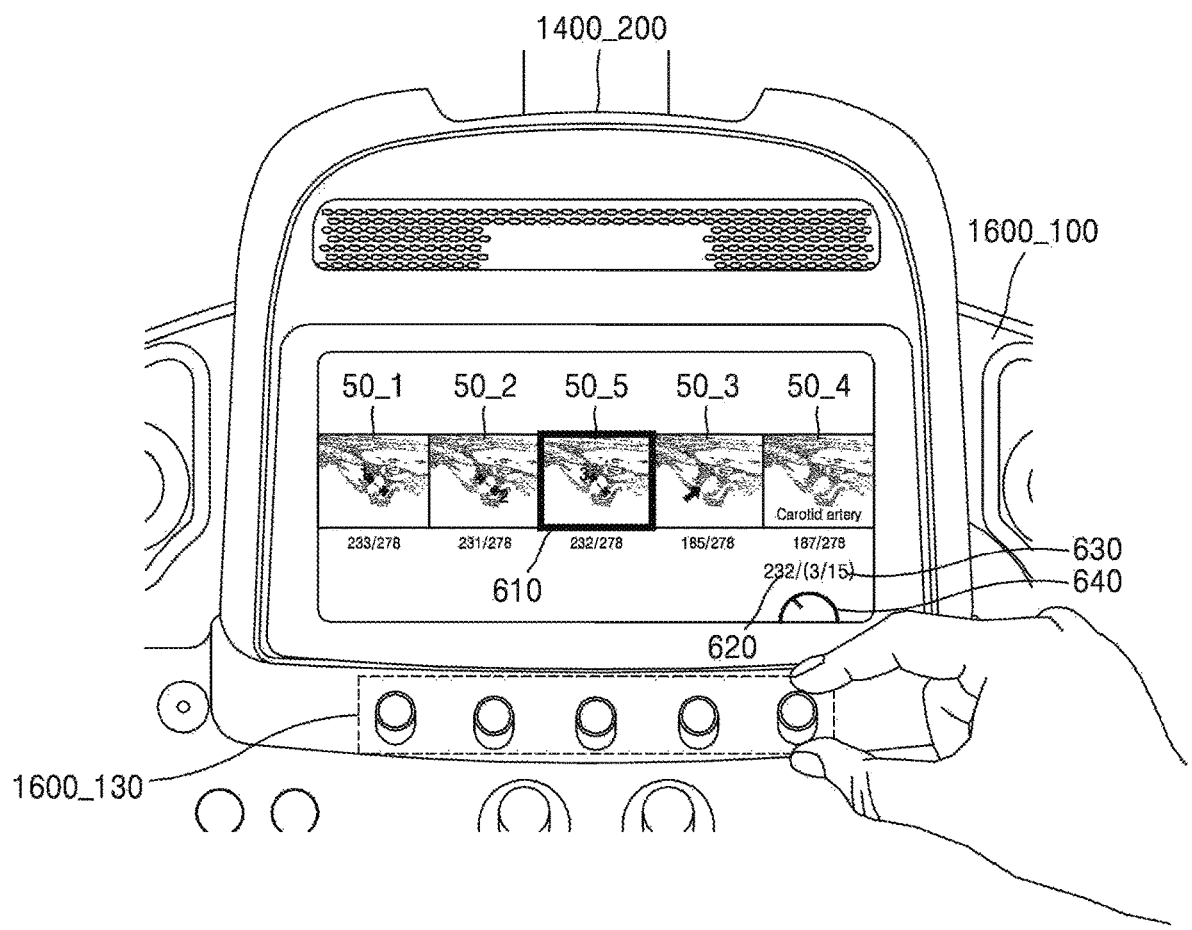
FIGS. 6A and 6B illustrate user interfaces (UIs) for selecting a reference frame, according to some exemplary embodiments.
Figure 6B:
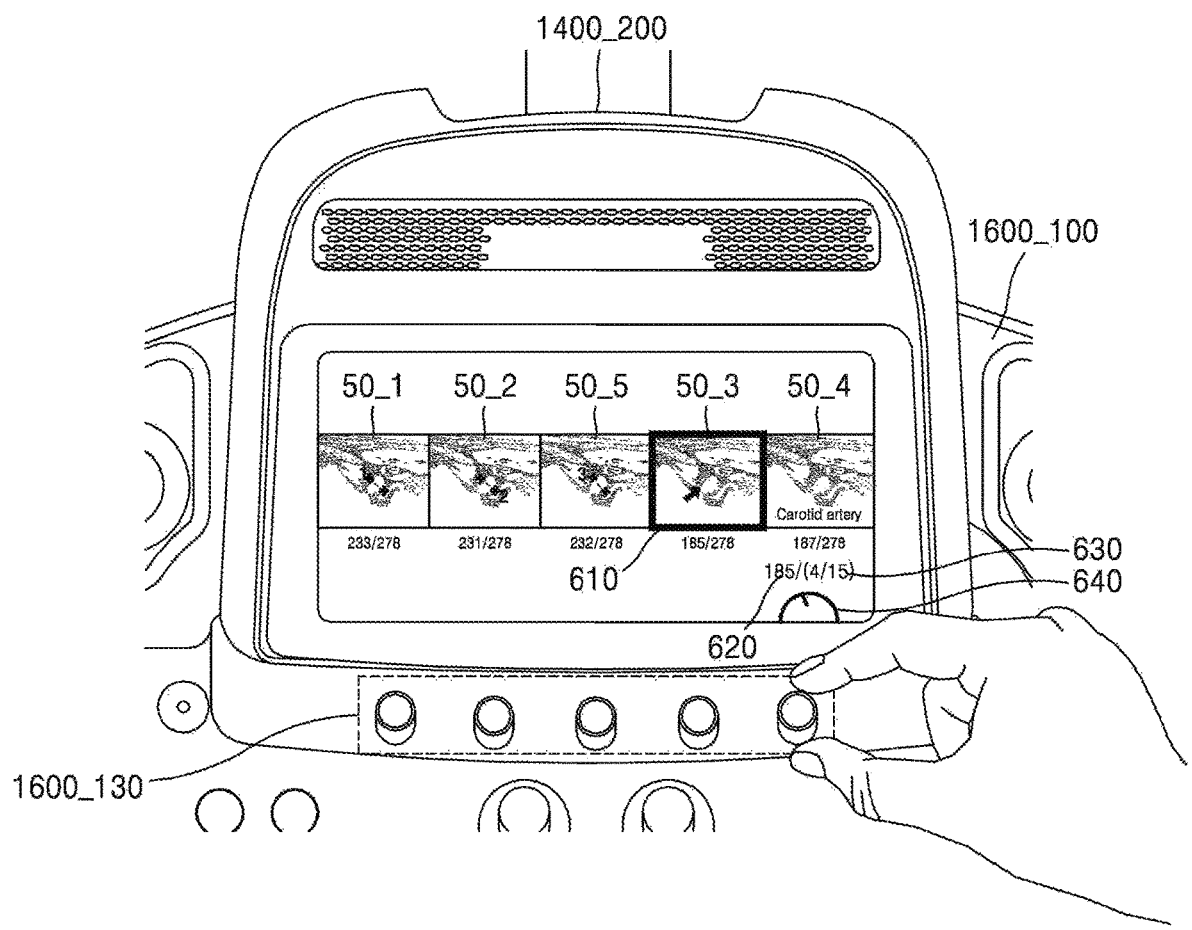

FIGS. 6A and 6B illustrate UIs for selecting a reference frame, according to some exemplary embodiments.

Referring to FIG. 6A, the ultrasound diagnosis apparatus 1000 may select one from the plurality of reference frames 50_1 through 50_5 in response to a user input of rotating one from among a plurality of knobs 1600_130.

The ultrasound diagnosis apparatus 1000 may include the plurality of knobs 1600_130 on the control panel 1600_100.

In response to a user input of rotating a preset one knob from among the plurality of knobs 1600_130, the ultrasound diagnosis apparatus 1000 may select one from the plurality of reference frames 50_1 through 50_5.

In response to a user input of rotating a knob, the ultrasound diagnosis apparatus 1000 may display a marker 610 representing the selected reference frame, on the selected reference frame 50_5.

In response to the user input of rotating a knob, the ultrasound diagnosis apparatus 1000 may also display a marker 630 representing a location of the reference frame selected from the plurality of reference frames. For example, when 15 reference frames are generated and the selected reference frame 50_5 is located at a third position, the ultrasound diagnosis apparatus 1000 may display "(3/15)". The ultrasound diagnosis apparatus 1000 may display a marker 620 representing a capturing order of the selected reference frame.

In response to the user input of rotating a knob, the ultrasound diagnosis apparatus 1000 may also display a marker 640 representing that the knob has been rotated.

In response to the user input of rotating a knob, the ultrasound diagnosis apparatus 1000 may sequentially select the plurality of reference frames 50_1 through 505.

For example, referring to FIG. 6B, when the reference frame 50_5 has been selected from the plurality of reference frames 50_1 through 50_5, the ultrasound diagnosis apparatus 1000 may select a reference frame 50_3 next to the selected reference frame 50_5, in response to a user input of rotating the knob right. In response to the user input of rotating the knob left, the ultrasound diagnosis apparatus 1000 may select a reference frame 50_2 previous to the selected reference frames 50_5.

Figure 7:
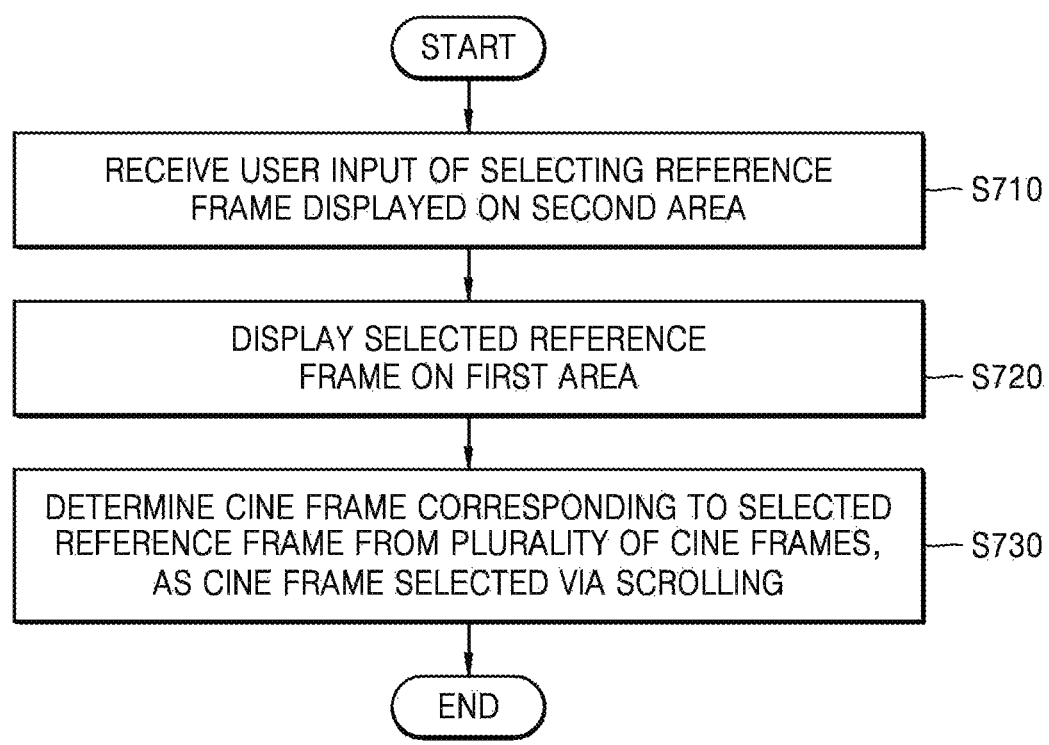
FIG. 7 is a flowchart of an exemplary embodiment in which the ultrasound diagnosis apparatus displays a selected reference frame in response to a user input of selecting a reference frame.

FIG. 7 is a flowchart of an exemplary embodiment in which the ultrasound diagnosis apparatus 1000 displays a selected reference frame in response to a user input of selecting a reference frame.

In operation S710, the ultrasound diagnosis apparatus 1000 may receive a user input of selecting a reference frame displayed on the second area.

For example, the ultrasound diagnosis apparatus 1000 may receive an input of clicking one from among a plurality of reference frames displayed on the second area, and may receive a touch input of selecting one from the plurality of reference frames. The ultrasound diagnosis apparatus 1000 may receive a user input of rotating a knob.

In operation S720, the ultrasound diagnosis apparatus 1000 may display the selected reference frame on a first area.

The ultrasound diagnosis apparatus 1000 may display the selected reference frame on the first area on which a selected cine frame is displayed.

In operation S730, the ultrasound diagnosis apparatus 1000 may determine a cine frame corresponding to the selected reference frame from a plurality of cine frames, as a cine frame selected via scrolling.

Thus, even when a user does not perform scrolling, the user may move to the cine frame to which the user has inputted additional information.

Figure 8A:
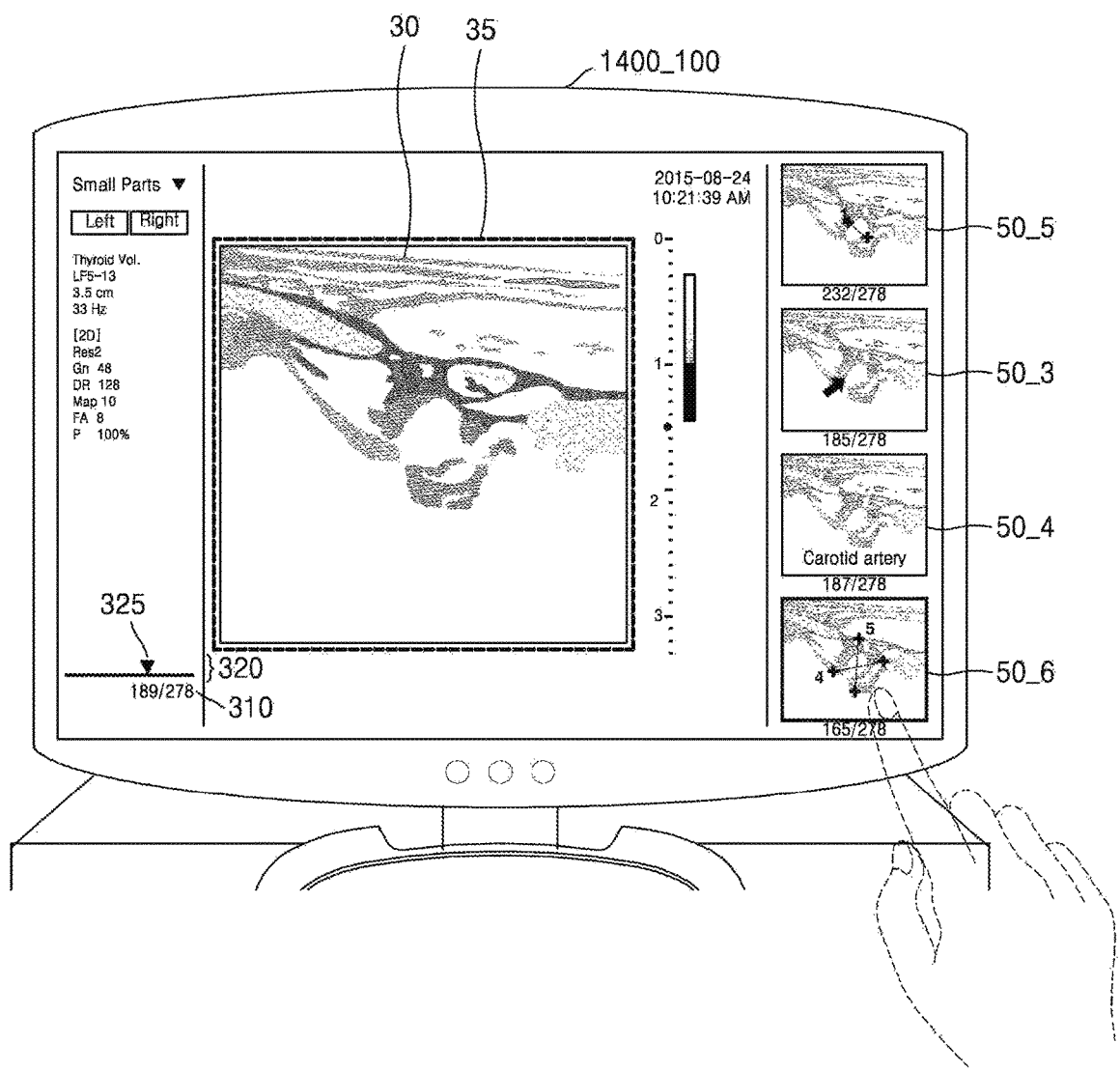
FIGS. 8A and 8B illustrate exemplary embodiments in which the ultrasound diagnosis apparatus displays a selected reference frame in response to a user input of selecting a reference frame.
Figure 8B:
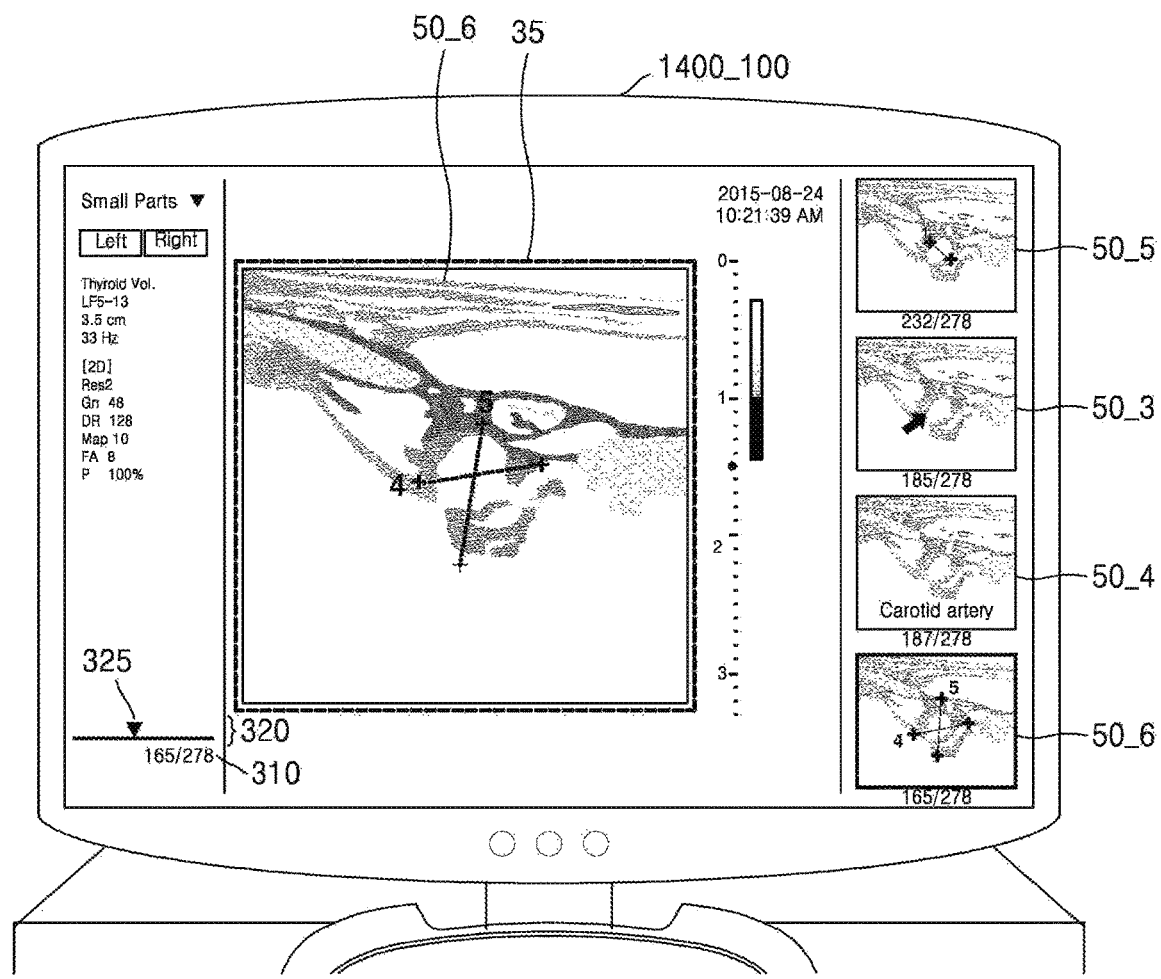

FIGS. 8A and 8B illustrate exemplary embodiments in which the ultrasound diagnosis apparatus 1000 displays a selected reference frame in response to a user input of selecting a reference frame.

Referring to FIG. 8A, the ultrasound diagnosis apparatus 1000 may display a plurality of reference frames 50_3 through 50_6.

The plurality of reference frames 50_3 through 50_6 may be generated and displayed by the ultrasound diagnosis apparatus 1000 in response to a user input of inputting additional information to a cine frame.

The ultrasound diagnosis apparatus 1000 may display the selected cine frame 30 in response to a user input of selecting one cine frame by scrolling a plurality of cine frames. As shown in FIG. 8A, the selected cine frame 30 may be a 189th cine frame from among 278 cine frames.

The ultrasound diagnosis apparatus 1000 may receive a user input of selecting the reference frame 50_6 from the plurality of reference frames 50_3 through 50_6.

Referring to FIG. 8B, in response to the user input of selecting the reference frame 50_6 from the plurality of reference frames 50_3 through 50_6, the ultrasound diagnosis apparatus 1000 may display the selected reference frame 50_6 on the first area 35 on which the cine frame was displayed.

The ultrasound diagnosis apparatus 1000 may determine a cine frame corresponding to the selected reference frame 50_6 from the plurality of cine frames, as a cine frame selected via scrolling. Since the selected reference frame 50_6 is generated from a 165th cine frame, the cine frame corresponding to the selected reference frame 50_6 may be the 165th cine frame. Accordingly, the ultrasound diagnosis apparatus 1000 may determine the 165th cine frame as a cine frame selected by scrolling.

When the 165th cine frame has been determined as the cine frame selected via scrolling, in response to a user input of scrolling the plurality of cine frames, the ultrasound diagnosis apparatus 1000 may sequentially display cine frames next or previous to the 165th cine frame on the first area.

As the 165th cine frame is determined as the cine frame selected via scrolling, the ultrasound diagnosis apparatus 1000 may change a marker (e.g., 310 or 320) representing a capturing order of the selected cine frame. For example, the ultrasound diagnosis apparatus 1000 may change a numeral representing the capturing order of the selected cine frame from 189 to 165. The ultrasound diagnosis apparatus 1000 may move a location marker 325 to the left.

Figure 9:
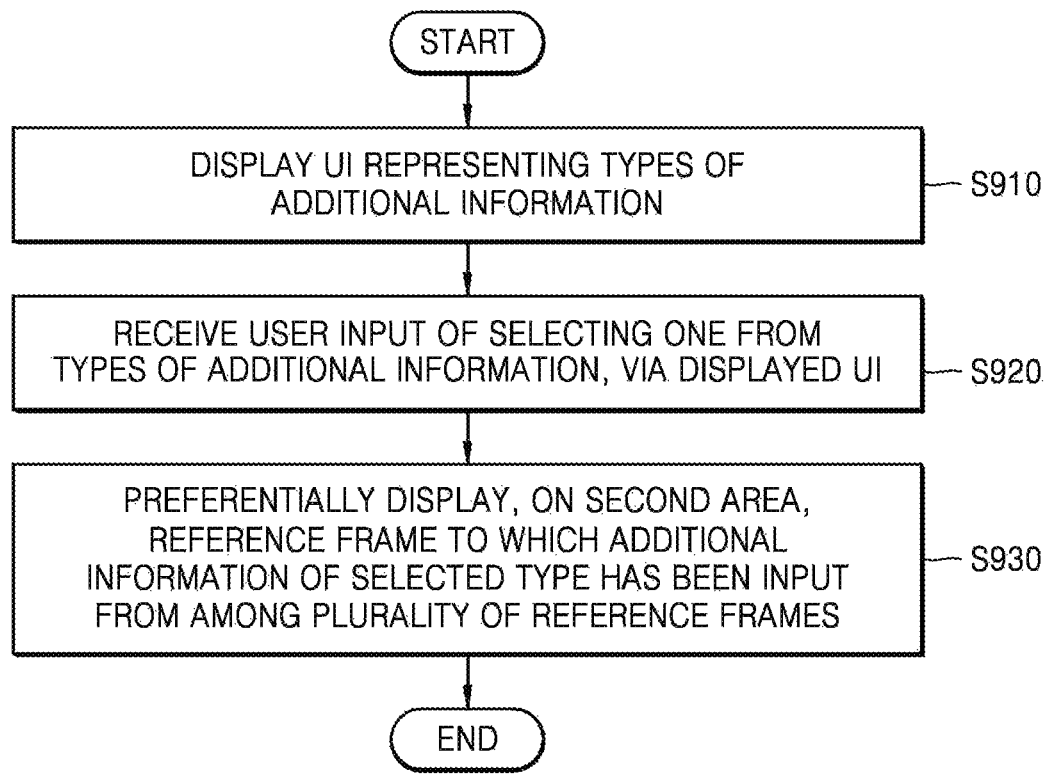
FIG. 9 is a flowchart of an exemplary embodiment in which the ultrasound diagnosis apparatus receives a user input of selecting one from a plurality of types of additional information and preferentially displays a reference frame to which additional information of the selected type has been input.

FIG. 9 is a flowchart of an exemplary embodiment in which the ultrasound diagnosis apparatus 1000 receives a user input of selecting one from a plurality of types of additional information and preferentially displays a reference frame to which additional information of the selected type has been input.

In operation S910, the ultrasound diagnosis apparatus 1000 may display a UI representing types of additional information.

The ultrasound diagnosis apparatus 1000 may display a UI for selecting one from a plurality of types of additional information, together with a plurality of reference frames.

The types of additional information may include measurement additional information and comment additional information. The measurement additional information may denote additional information input onto a cine frame by measuring a target within the cine frame. The comment additional information may denote detailed information about the target that has been input to the cine frame by a user.

The measurement additional information may be additional information about a distance, a width, a length, a volume, a ratio, or an angle. The comment additional information may be a text comment, a body marker, an arrow, or the like.

In operation S920, the ultrasound diagnosis apparatus 1000 may receive a user input of selecting one from the plurality of types of additional information, via the displayed UI.

In operation S930, the ultrasound diagnosis apparatus 1000 may preferentially display, on the second area, a reference frame to which additional information of the selected type has been input from among the plurality of reference frames.

The ultrasound diagnosis apparatus 1000 may preferentially display the reference frame to which the additional information of the selected type has been input, more prominently than the other frames. For example, the ultrasound diagnosis apparatus 1000 may display the reference frame to which the additional information of the selected type has been input, on an uppermost portion of the second area such that the reference frame is displayed first. The ultrasound diagnosis apparatus 1000 may display the reference frame to which the additional information of the selected type has been input, at a location the closest to the cine frame such that the reference frame is the most prominent.

Figure 10A:
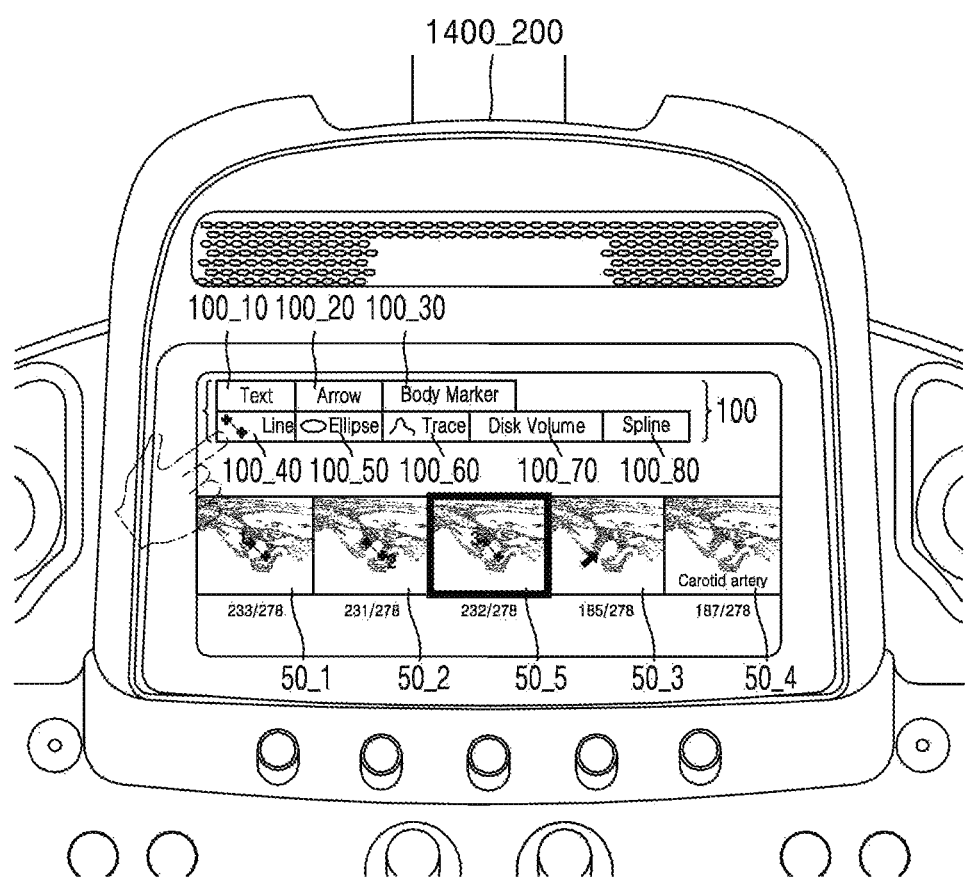
FIGS. 10A and 10B illustrate an exemplary embodiment in which the ultrasound diagnosis apparatus receives a user input of selecting one from a plurality of types of additional information and preferentially displays a reference frame to which additional information of the selected type has been input.
Figure 10B:
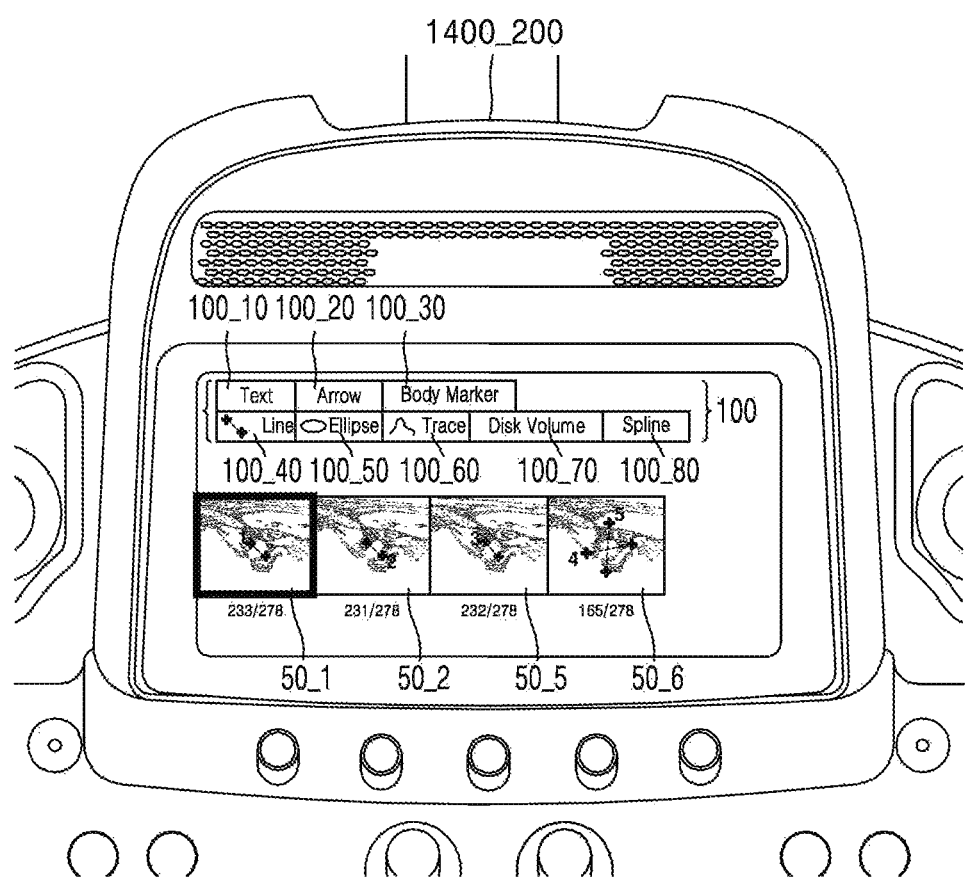

FIGS. 10A and 10B illustrate an exemplary embodiment in which the ultrasound diagnosis apparatus 1000 receives a user input of selecting one from a plurality of types of additional information and preferentially displays a reference frame to which additional information of the selected type has been input.

Referring to FIG. 10A, the ultrasound diagnosis apparatus 1000 may display a UI 100 for selecting one from a plurality of types of additional information.

The UI 100 for selecting one from a plurality of types of additional information may include a plurality of buttons 100_10 through 100_80 respectively representing the types of the additional information.

The ultrasound diagnosis apparatus 1000 may receive a user input of selecting the button 100_40 for selecting additional information related with a length measurement from the plurality of buttons 100_10 through 100_80.

Referring to FIG. 10B, in response to the user input of selecting the button 100_40 for selecting additional information related with a length measurement, the ultrasound diagnosis apparatus 1000 may display a reference frame to which the additional information related with a length measurement has been input from among the plurality of reference frames. The ultrasound diagnosis apparatus 1000 may display only reference frames 50_1, 50_2, 50_5, and 50_6 to which the additional information related with a length measurement has been input, on a second area of the screen. In some cases, the ultrasound diagnosis apparatus 1000 may preferentially display the reference frames 50_1, 50_2, 50_5, and 50_6 to which the additional information related with a length measurement has been input, than the other frames.

Thus, a user is able to observe only a reference frame to which additional information of a desired type has been input and to compare input reference frames to which additional information of the same type has been input with one another.

Figure 11A:
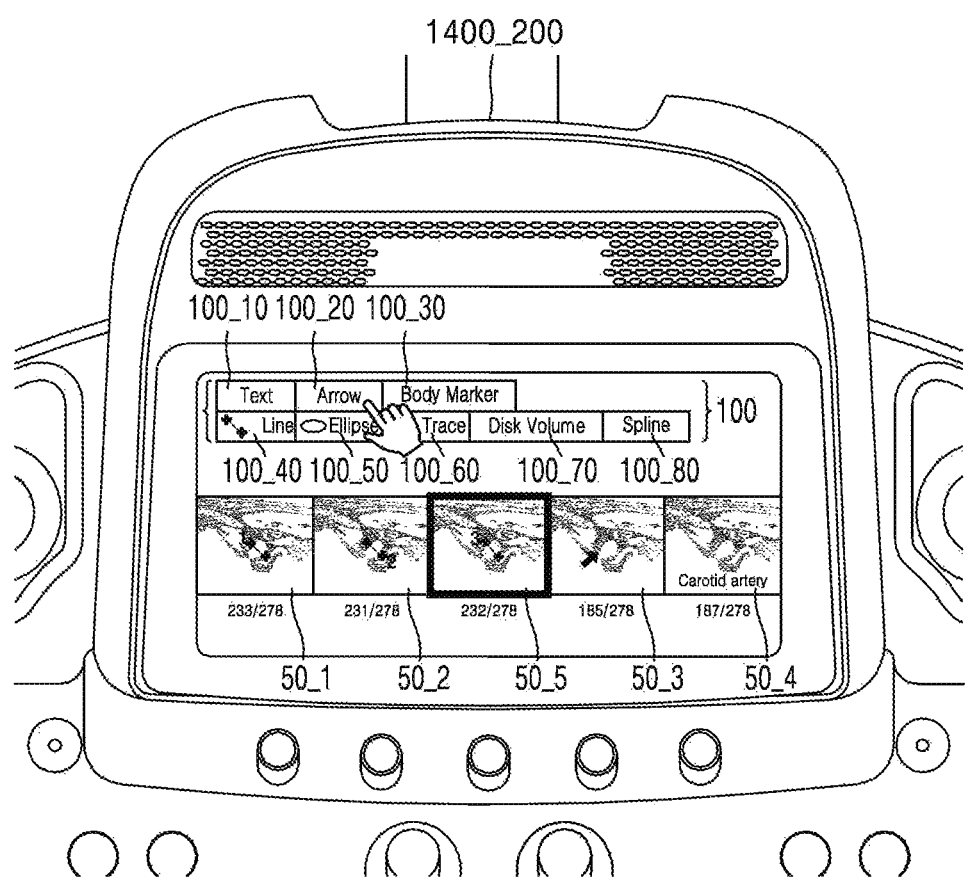
FIGS. 11A and 11B illustrate another exemplary embodiment in which the ultrasound diagnosis apparatus receives a user input of selecting one from a plurality of types of additional information and preferentially displays a reference frame to which additional information of the selected type has been input.
Figure 11B:
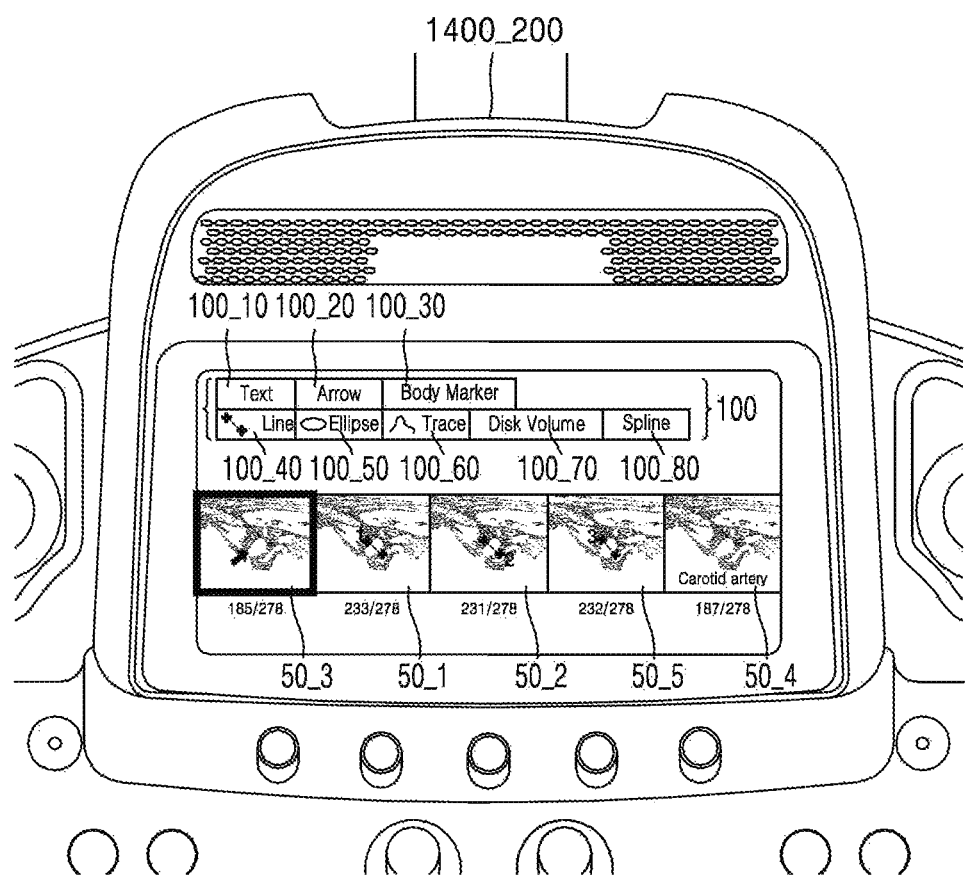

FIGS. 11A and 11B illustrate another exemplary embodiment in which the ultrasound diagnosis apparatus 1000 receives a user input of selecting one from a plurality of types of additional information and preferentially displays a reference frame to which additional information of the selected type has been input.

Referring to FIG. 11A, the ultrasound diagnosis apparatus 1000 may receive a user input of selecting an arrow comment 100_2 from a plurality of types of additional information 100_10 through 100_80.

Referring to FIG. 11B, in response to the user input of selecting the arrow comment 100_20, the ultrasound diagnosis apparatus 1000 may preferentially display a reference frame 50_3 to which an arrow comment has been input from among a plurality of reference frames.

For example, as shown in FIG. 11B, the ultrasound diagnosis apparatus 1000 may display the reference frame 50_3 to which an arrow_has been input, in the very front of displayed reference frames.

Figure 12:
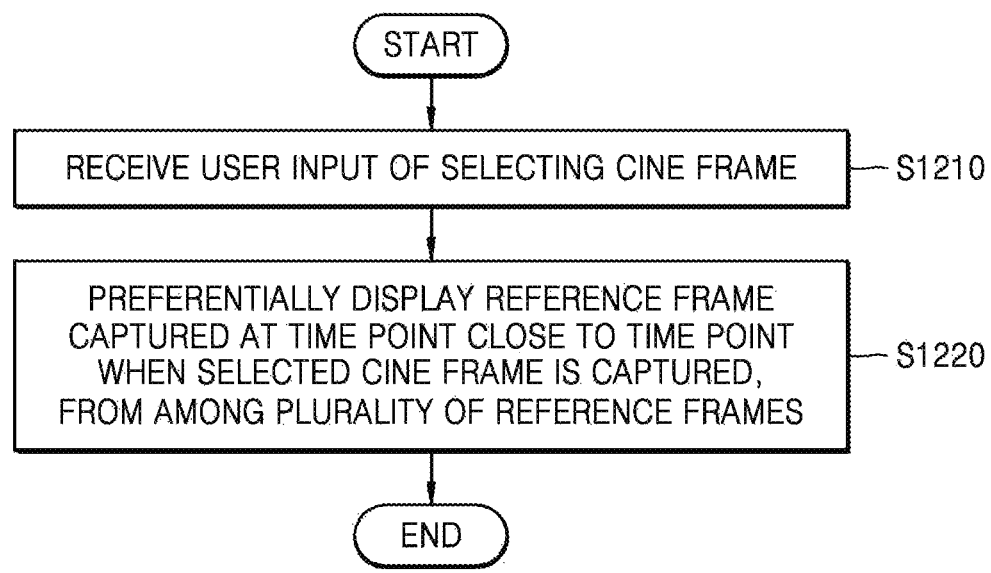
FIG. 12 is a flowchart of an exemplary embodiment in which the ultrasound diagnosis apparatus preferentially displays a reference frame captured at a time point close to a time point when a selected cine frame has been captured.

FIG. 12 is a flowchart of an exemplary embodiment in which the ultrasound diagnosis apparatus 1000 preferentially displays a reference frame captured at a time point close to the time point when a selected cine frame has been captured.

In operation S1210, the ultrasound diagnosis apparatus 1000 may receive a user input of selecting a cine frame.

Operation S1210 may be understood with reference to operation S210 of FIG. 2.

In operation S1220, the ultrasound diagnosis apparatus 1000 may preferentially display a reference frame captured at a time point close to the time point when the selected cine frame is captured, from among a plurality of reference frames.

In response to the user input of selecting a cine frame, the ultrasound diagnosis apparatus 1000 may determine reference frames captured at time points close to the time point when the selected cine frame has been captured from among the plurality of reference frames, and may display the determined reference frames in the order of capturing time points.

Figure 13:
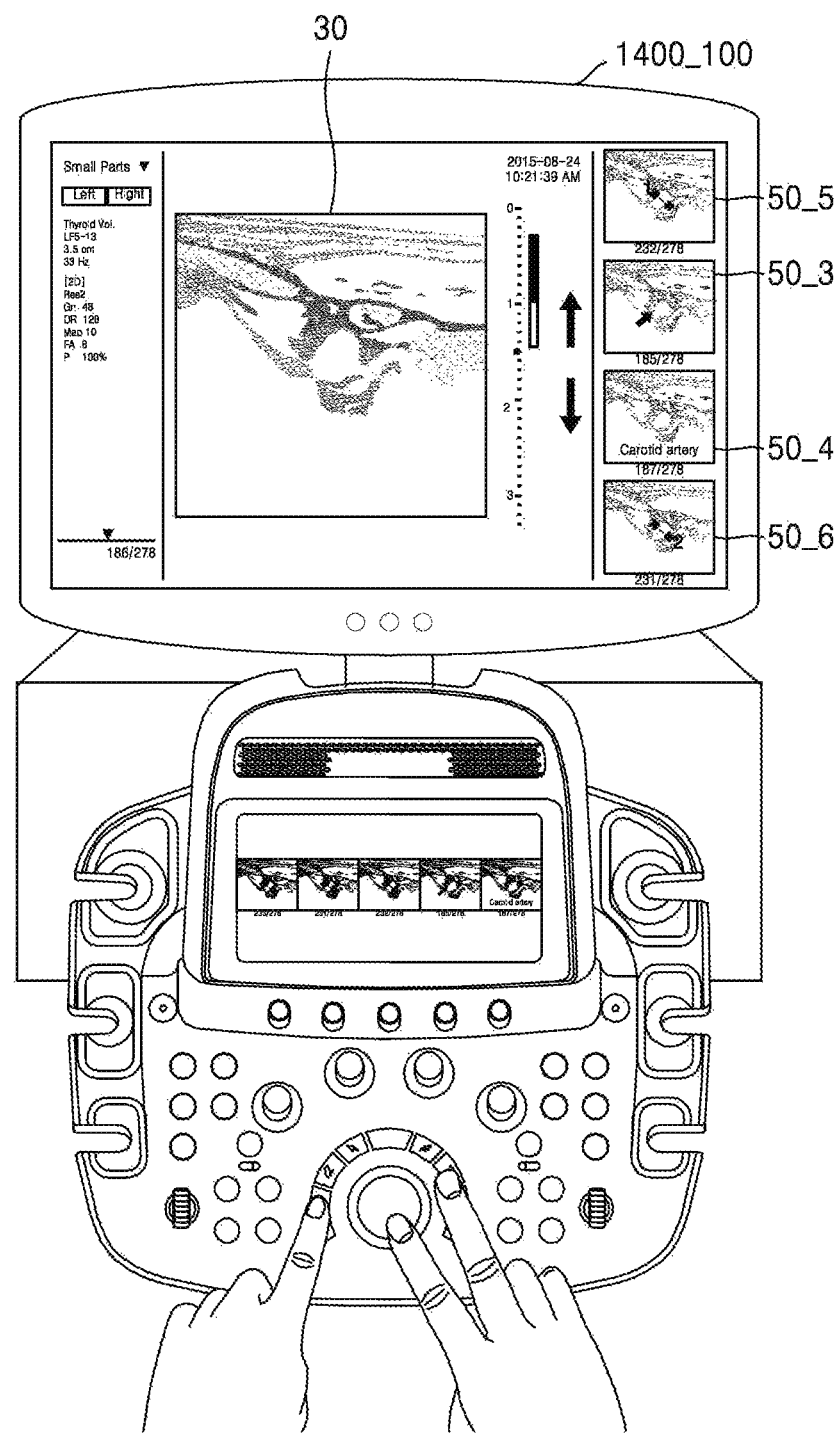
FIG. 13 illustrates an exemplary embodiment in which the ultrasound diagnosis apparatus preferentially displays a reference frame captured at a time point close to a time point when a selected cine frame has been captured.

FIG. 13 illustrates an exemplary embodiment in which the ultrasound diagnosis apparatus 1000 preferentially displays a reference frame captured at a time point close to the time point when a selected cine frame has been captured.

Referring to FIG. 13, in response to a user input of selecting a cine frame, the ultrasound diagnosis apparatus 1000 may preferentially display a reference frame captured at a time point close to the time point when the selected cine frame has been captured from among a plurality of reference frames.

For example, in response to a user input of selecting a 186th cine frame 30 by scrolling a plurality of cine frames, the ultrasound diagnosis apparatus 1000 may preferentially display a reference frame captured at a time point close to the time point when the 186th cine frame has been captured.

For example, the ultrasound diagnosis apparatus 1000 may display reference frames captured at time points close to the time point when the 186th cine frame was captured, such that reference frames whose capturing time points are farther from the capturing time point of the 186th cine frame are arranged in a direction away from the center of the second area. For example, the ultrasound diagnosis apparatus 1000 may display a 185th reference frame closest to the $186^{th}$ cine frame from among reference frames earlier captured than the $186^{th}$ cine frame, on the center of the second area. The ultrasound diagnosis apparatus 1000 may display a 187th reference frame closest to the $186^{th}$ cine frame from among reference frames later captured than the $186^{th}$ cine frame, on the center of the second area.

Accordingly, a user may compare reference frames of which capturing time points are close to the capturing time point of a selected cine frame with the selected cine frame, and thus may check additional information input by the user onto a reference frame having a similar capturing direction or capturing body part to the selected cine frame.

Figure 14:
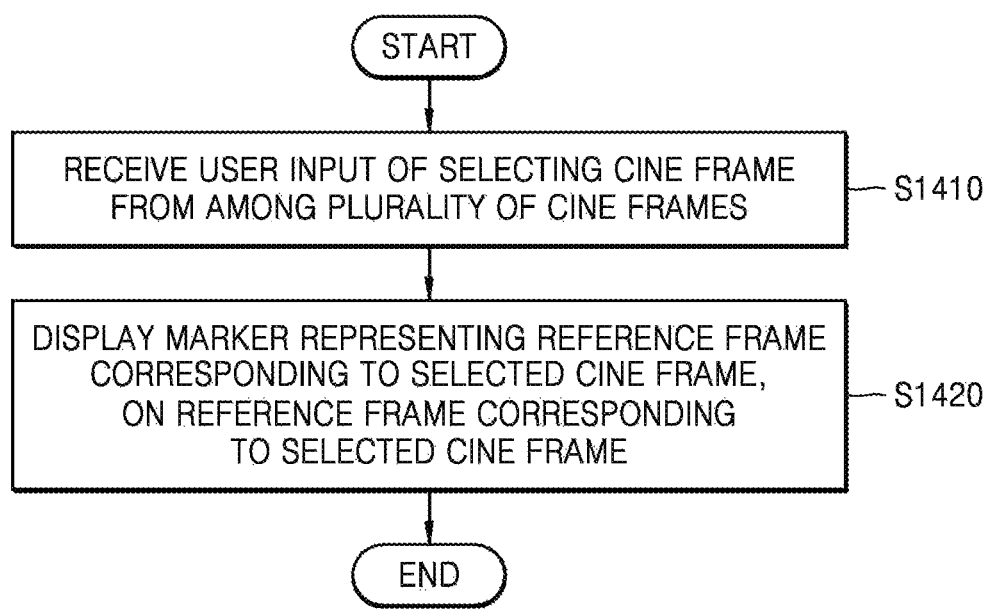
FIG. 14 is a flowchart of an exemplary embodiment in which the ultrasound diagnosis apparatus displays a marker representing a reference frame corresponding to a selected cine frame on the reference frame.

FIG. 14 is a flowchart of an exemplary embodiment in which the ultrasound diagnosis apparatus 1000 displays a marker representing a reference frame corresponding to a selected cine frame on the reference frame.

In operation S1410, the ultrasound diagnosis apparatus 1000 may receive a user input of selecting a cine frame from among a plurality of cine frames.

Operation S1410 may be understood with reference to operation S210 of FIG. 2.

In operation S1420, the ultrasound diagnosis apparatus 1000 may display a marker representing a reference frame corresponding to the selected cine frame, on the reference frame corresponding to the selected cine frame.

The reference frame corresponding to the selected cine frame may denote a reference frame generated from the selected cine frame.

In response to the user input of selecting one from the plurality of cine frames, the ultrasound diagnosis apparatus 1000 may determine whether reference frames corresponding to the selected cine frame exist. When a reference frame corresponding to the selected cine frame exists, the ultrasound diagnosis apparatus 1000 may display the reference frame corresponding to the selected cine frame on the second area and display a marker representing a reference frame corresponding to the selected cine frame, on the reference frame corresponding to the selected cine frame.

Figure 15:
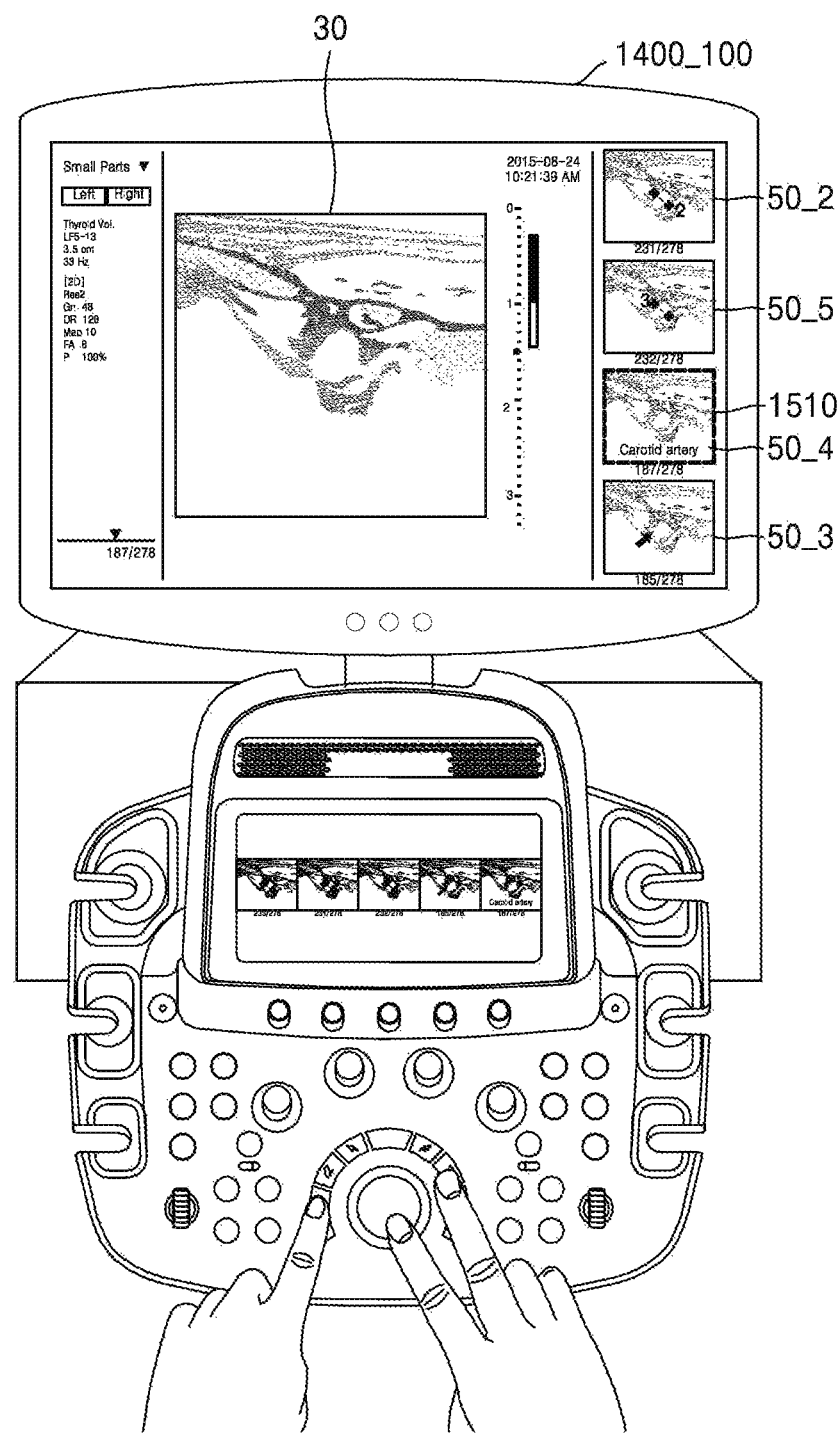
FIG. 15 illustrates an exemplary embodiment in which the ultrasound diagnosis apparatus displays a marker representing a reference frame corresponding to a selected cine frame on the reference frame.

FIG. 15 illustrates an exemplary embodiment in which the ultrasound diagnosis apparatus 1000 displays a marker representing a reference frame corresponding to a selected cine frame, on the reference frame.

Referring to FIG. 15, the ultrasound diagnosis apparatus 1000 may receive a user input of selecting a 187th cine frame 30 from among a plurality of cine frames.

In response to the user input of selecting the 187th cine frame 30, the ultrasound diagnosis apparatus 1000 may determine a reference frame 50_4 corresponding to the 187th cine frame 30 from among a plurality of reference frames. The reference frame 50_4 corresponding to the 187th cine frame 30 may be a reference frame obtained by inputting a text comment "Carotid artery" to the 187th cine frame 30.

As the reference frame 50_4 corresponding to the 187th cine frame 30 is determined, the ultrasound diagnosis apparatus 1000 may display the determined reference frame 50_4 on the second area. The ultrasound diagnosis apparatus 1000 may display a marker 1510 representing a reference frame corresponding to the 187th cine frame 30, on the determined reference frame 50_4.

Accordingly, a user may check additional information input onto the selected cine frame.

Figure 16:
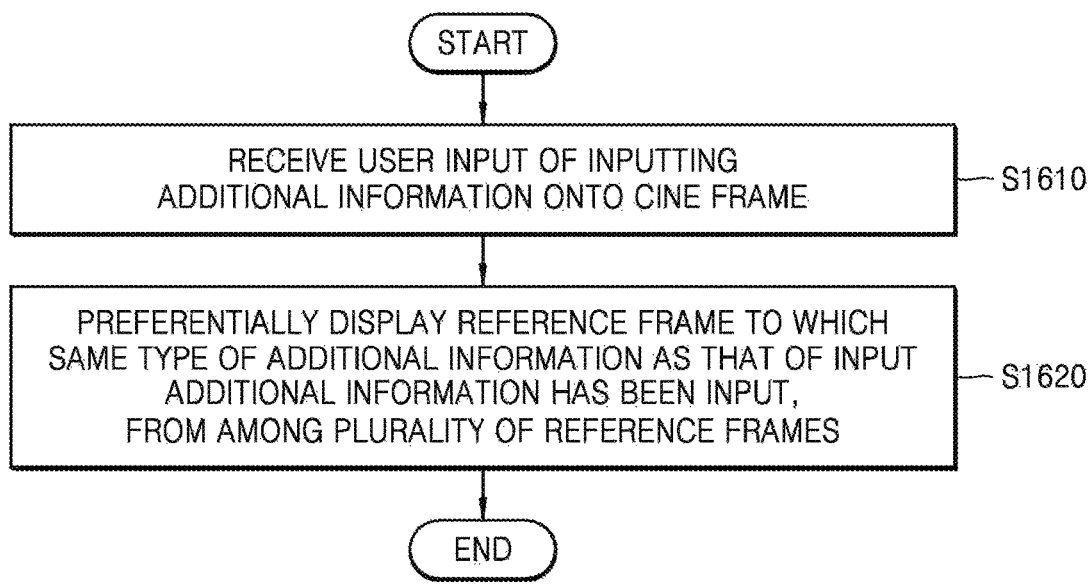
FIG. 16 is a flowchart of an exemplary embodiment in which the ultrasound diagnosis apparatus preferentially displays a reference frame to which the same type of additional information as that of additional information input to a cine frame has been input.

FIG. 16 is a flowchart of an exemplary embodiment in which the ultrasound diagnosis apparatus 1000 preferentially displays a reference frame to which the same type of additional information as that of additional information input to a cine frame has been input.

In operation S1610, the ultrasound diagnosis apparatus 1000 may receive a user input of inputting additional information onto a cine frame.

Operation S1610 may be understood with reference to operation S210 of FIG. 2.

In operation S1620, the ultrasound diagnosis apparatus 1000 may preferentially display a reference frame to which the same type of additional information as that of the additional information input to the cine frame has been input, from among a plurality of reference frames.

For example, in response to a user input of selecting a button for inputting additional information, the ultrasound diagnosis apparatus 1000 may preferentially display a reference frame to which the same type of additional information as that of the additional information input to the cine frame has been input, from among a plurality of reference frames.

Figure 17:
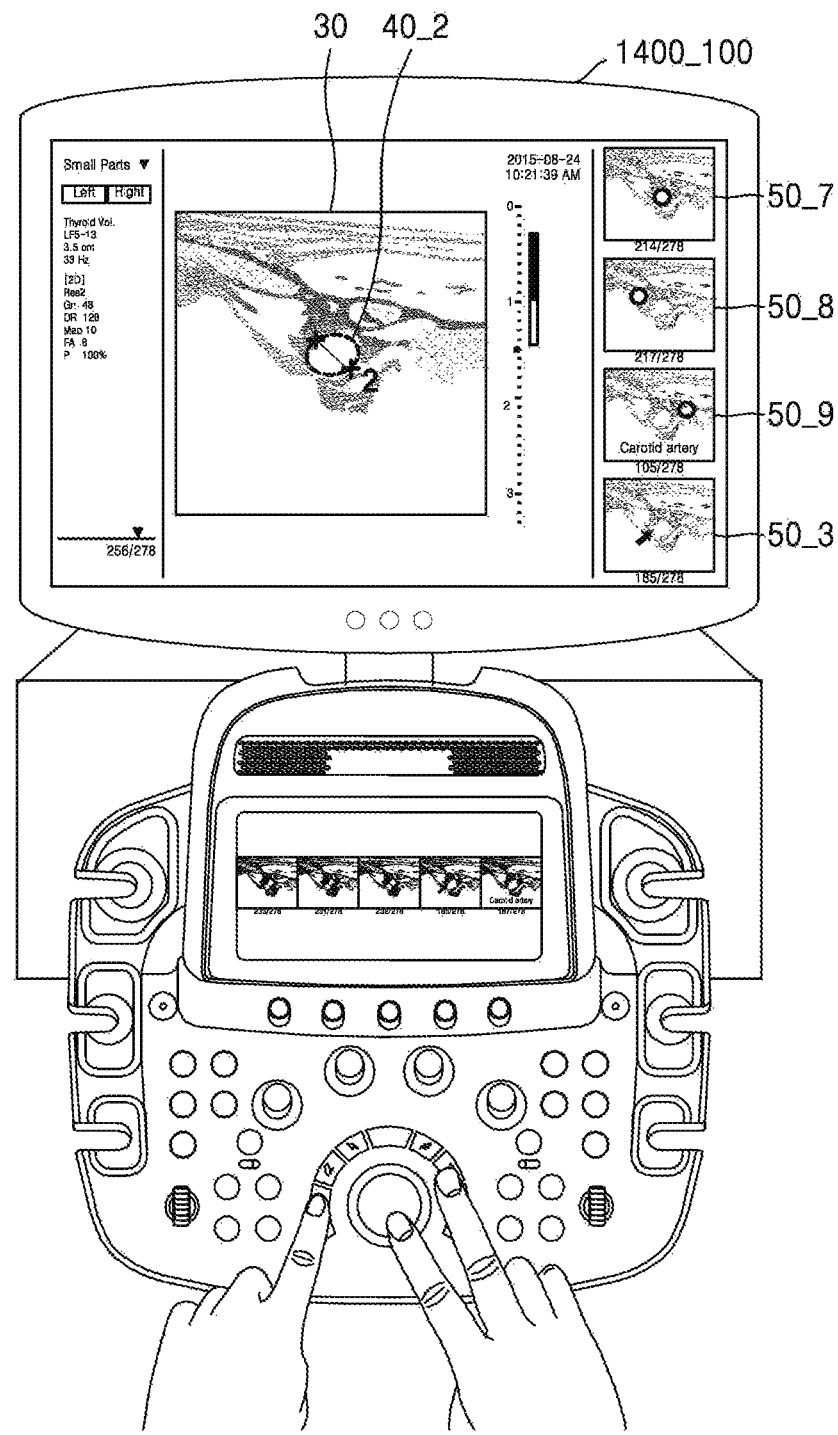
FIG. 17 illustrates an exemplary embodiment in which the ultrasound diagnosis apparatus preferentially displays a reference frame to which the same type of additional information as that of additional information input to a cine frame has been input.

FIG. 17 illustrates an exemplary embodiment in which the ultrasound diagnosis apparatus 1000 preferentially displays a reference frame to which the same type of additional information as that of additional information input to a cine frame has been input.

Referring to FIG. 17, the ultrasound diagnosis apparatus 1000 may receive a user input of measuring an oval region of a target within a cine frame 30.

The user input of measuring the oval region of the target may include a user input of selecting a button for setting an oval 40_2 on the cine frame 30. The user input of measuring the oval region of the target may be a user input of setting a location of the oval 40_2 or may be a user input of adjusting the size of the oval 40_2.

In response to the user input of measuring the oval region, the ultrasound diagnosis apparatus 1000 may preferentially display reference frames 50_7, 50_8, and 50_9 generated by measuring the oval region.

For example, the ultrasound diagnosis apparatus 1000 may display the generated reference frames 50_7, 50_8, and 50_9 on an upper end or right end of the second area.

Figure 18:
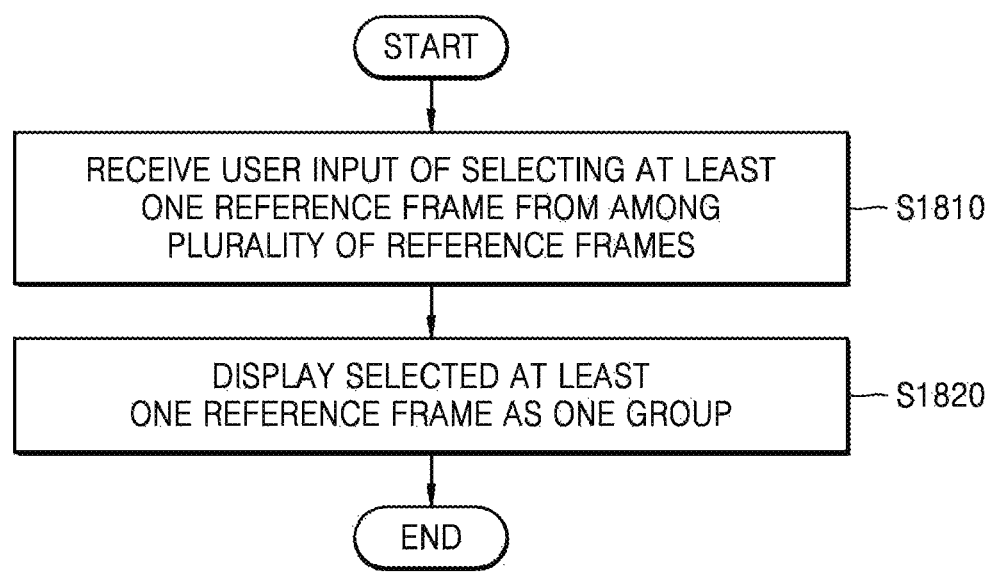
FIG. 18 is a flowchart of an exemplary embodiment in which the ultrasound diagnosis apparatus displays reference frames selected by a user from a plurality of reference frames, as a group.

FIG. 18 is a flowchart of an exemplary embodiment in which the ultrasound diagnosis apparatus 1000 displays reference frames selected by a user from a plurality of reference frames, as a group.

In operation S1810, the ultrasound diagnosis apparatus 1000 may receive a user input of selecting at least one reference frame from among a plurality of reference frames.

The ultrasound diagnosis apparatus 1000 may display a UI for selecting the at least one reference frame from among the plurality of reference frames.

In operation S1820, the ultrasound diagnosis apparatus 1000 may display the selected at least one reference frame as a group.

As the ultrasound diagnosis apparatus 1000 receives the user input of selecting the at least one reference frame via the UI for selecting the at least one reference frame, the ultrasound diagnosis apparatus 1000 may display the selected at least one reference frame as a group.

For example, the ultrasound diagnosis apparatus 1000 may display the selected at least one reference frame on the first area. The ultrasound diagnosis apparatus 1000 may preferentially display the selected at least one reference frame on the second area, more prominently than the other reference images. The ultrasound diagnosis apparatus 1000 may display the selected at least one reference frame on a third area other than the first and second areas.

The ultrasound diagnosis apparatus 1000 may store the selected at least one reference frame in a separate group. In this case, the ultrasound diagnosis apparatus 1000 may receive a user input of inputting ID information of the group.

Figure 19A:
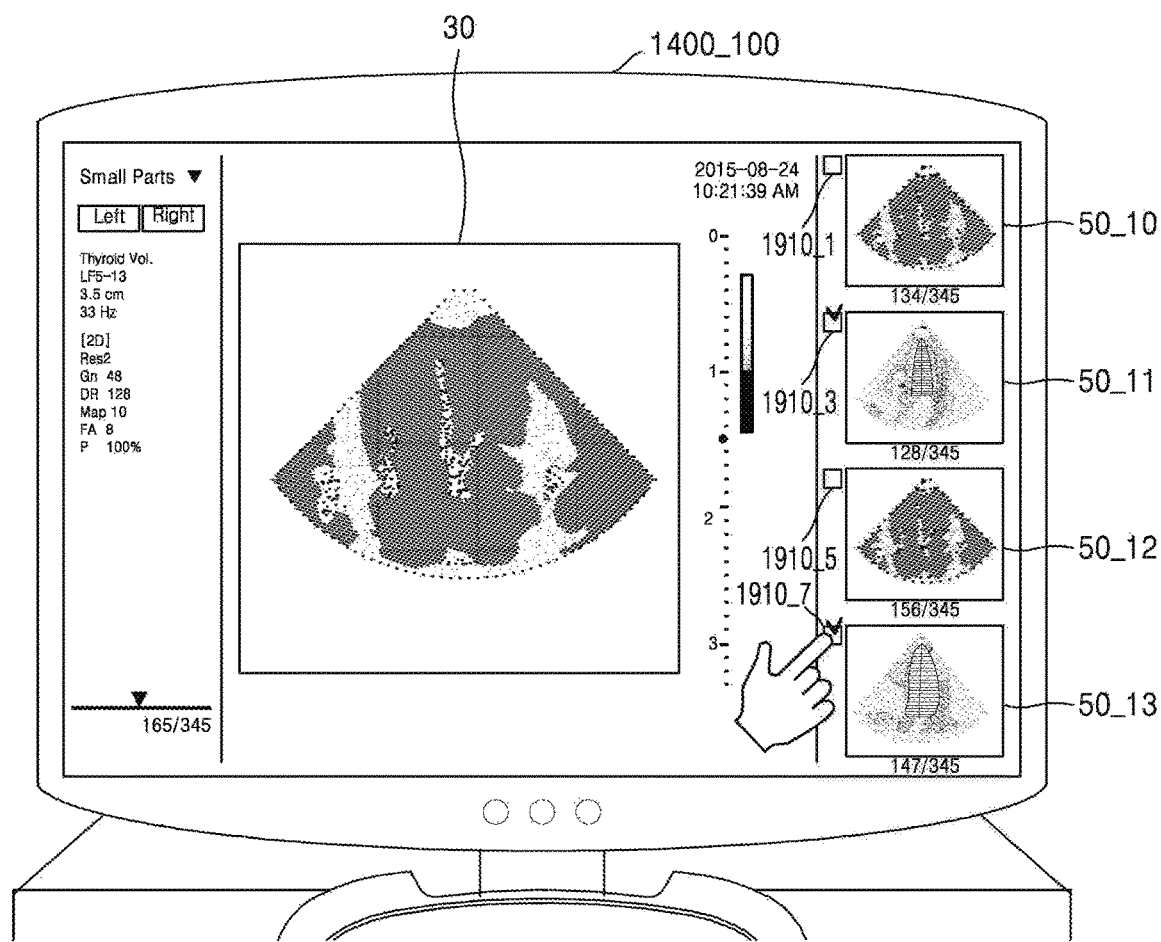
FIGS. 19A and 19B illustrate an exemplary embodiment in which the ultrasound diagnosis apparatus displays reference frames selected by a user from a plurality of reference frames, as a group.
Figure 19B:
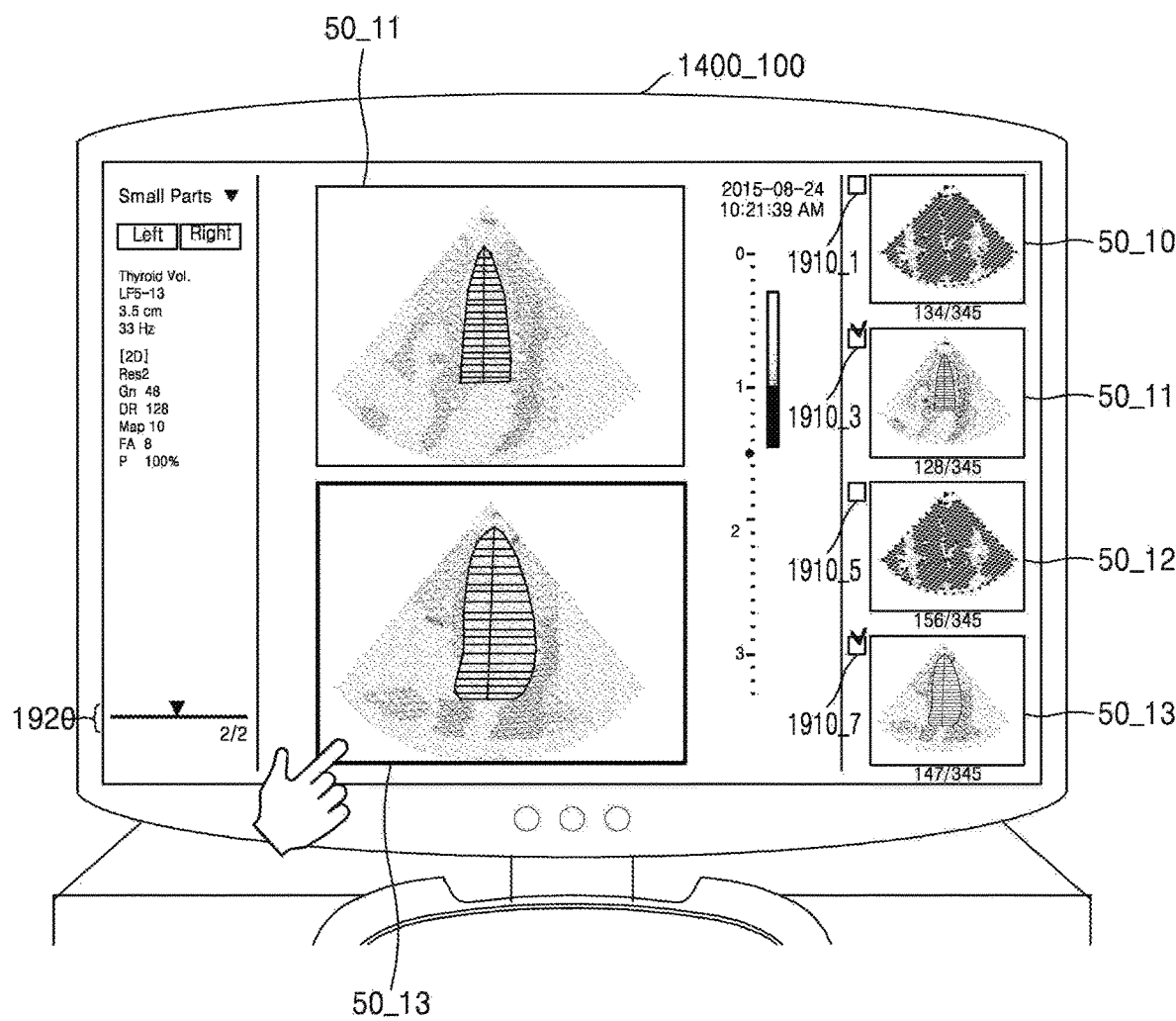

FIGS. 19A and 19B illustrate an exemplary embodiment in which the ultrasound diagnosis apparatus 1000 displays reference frames selected by a user from a plurality of reference frames, as a group.

Referring to FIG. 19A, the ultrasound diagnosis apparatus 1000 may display UIs 1910_1, 1910_3, 1910_5, and 1910_7 for selecting at least one reference frame from among a plurality of reference frames 50_10, 50_11, 50_12, and 50_13.

For example, as shown in FIG. 19A, the UIs 1910_1, 1910_3, 1910_5, and 1910_7 for selecting at least one reference frame from among the plurality of reference frames 50_10, 50_11, 50_12, and 50_13 may be check boxes enabling respective reference frames corresponding thereto to be selected.

Referring to FIG. 19B, as the ultrasound diagnosis apparatus 1000 receives a user input of selecting a second reference frame 50_11 and a fourth reference frame 50_13 via the UIs 1910_1, 1910_3, 1910_5, and 1910_7, the ultrasound diagnosis apparatus 1000 may display the second and fourth reference frames 50_11 and 50_13 as a group.

In this case, the ultrasound diagnosis apparatus 1000 may display a marker 1920 representing the number of selected reference frames 50_11 and 50_13 and the order of a currently-focused reference frame 50_13 from among the selected reference frames 50_11 and 50_13.

Accordingly, a user may display only reference frames of interest from among the plurality of reference frames and compare the displayed reference frames of interest with one another.

Figure 20:
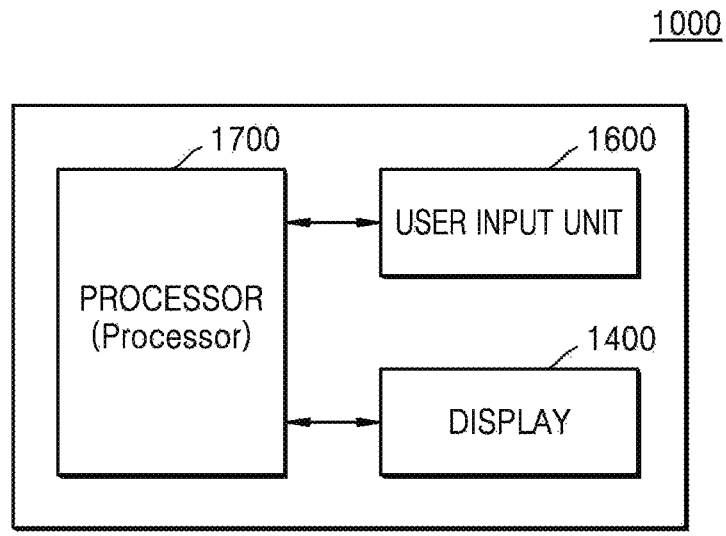
FIG. 20 is a block diagram of a structure of the ultrasound diagnosis apparatus, according to an exemplary embodiment.

FIG. 20 is a block diagram of a structure of the ultrasound diagnosis apparatus 1000, according to an exemplary embodiment.

Referring to FIG. 20, the ultrasound diagnosis apparatus 100 may include a processor 1700, a user input unit 1600, and a display 1400.

However, all of the illustrated components are not essential. The ultrasound diagnosis apparatus 1000 may be implemented by more or less components than those illustrated in FIG. 20.

Although the user input unit 1600 and the display 1400 are illustrated in FIG. 20, the user input unit 1600 and the display 1400 may be integrated into one body as in a touch screen.

The display 1400 may display an ultrasound image or a UI. For example, the display 1400 may display a plurality of cine frames. The display 1400 may display a first cine frame selected by a user from a plurality of cine frames, on a first area on the screen of the display 1400.

In some cases, the display 1400 may include the main display 1400_100 and the sub-display 1400_200.

The user input unit 1600 may receive a user input for manipulating the ultrasound diagnosis apparatus 1000. For example, the user input unit 1600 may receive a user input of inputting additional information onto the displayed first cine frame.

The processor 1700 may control overall components of the ultrasound diagnosis apparatus 1000. For example, the processor 1700 may generate a reference frame, based on input additional information and the first cine frame. The processor 1700 may control the display 1400 to display the generated reference frame on a second area of the screen.

The user input unit 1600 may receive a user input of selecting the reference frame displayed on the second area. The processor 1700 may also control the display 1400 to display the selected reference frame on the first area.

The user input unit 1600 may receive a user input of selecting a second cine frame from the plurality of cine frames by scrolling the plurality of cine frames in the order of being captured, and a user input of selecting the reference frame displayed on the second area.

In response to a user input of selecting the reference frame displayed on the second area, the processor 1700 may change the selected cine frame from the second cine frame to the first cine frame corresponding to the selected reference frame.

The display 1400 may display a marker representing the capturing order of the selected cine frame. As the first cine frame is determined as a cine frame selected via scrolling, the display 1400 may change the displayed marker to a marker representing that the selected cine frame has changed from the second cine frame to the first cine frame, and display the changed marker.

The user input unit 1600 may include a knob. Accordingly, when a plurality of reference frames including the generated reference frame have been displayed on the second area, the user input unit 1600 may receive a user input of rotating the knob included in the ultrasound diagnosis apparatus 1000.

In response to the user input of rotating the knob, the processor 1700 may control the display 1400 so that the plurality of reference frames are sequentially selected.

The display 1400 may display a UI for selecting the type of additional information. When the plurality of reference frames including the generated reference frame have been displayed on the second area, the user input unit 1600 may receive a user input of selecting one from various types of additional information, via the UI. The processor 1700 may control the display 1400 to preferentially display, on the second area, a reference frame to which additional information of the selected type has been input from among the plurality of reference frames.

When the plurality of reference frames have been displayed on the second area and the processor 1700 receives a user input of selecting the first cine frame, the processor 1700 may control the display 140 to preferentially display a reference frame captured at a time point close to the time point when the selected first cine frame is captured, from among the plurality of reference frames.

The user input unit 1600 may receive a user input of re-selecting the first cine frame from the plurality of cine frames by scrolling the plurality of cine frames in the capturing order. As the first cine frame is re-selected, the processor 1700 may control the display 1400 to display, on the reference frame displayed on the second area, a marker representing that the reference frame displayed on the second area is a reference frame corresponding to the first cine frame.

When the plurality of reference frames including the generated reference frame have been displayed on the second area and the processor 1700 receives a user input of inputting additional information onto the first cine frame, the processor 1700 may control the display 140 to preferentially display a reference frame to which the same type of additional information as that of the input additional information has been input, from among the plurality of reference frames.

Figure 21:
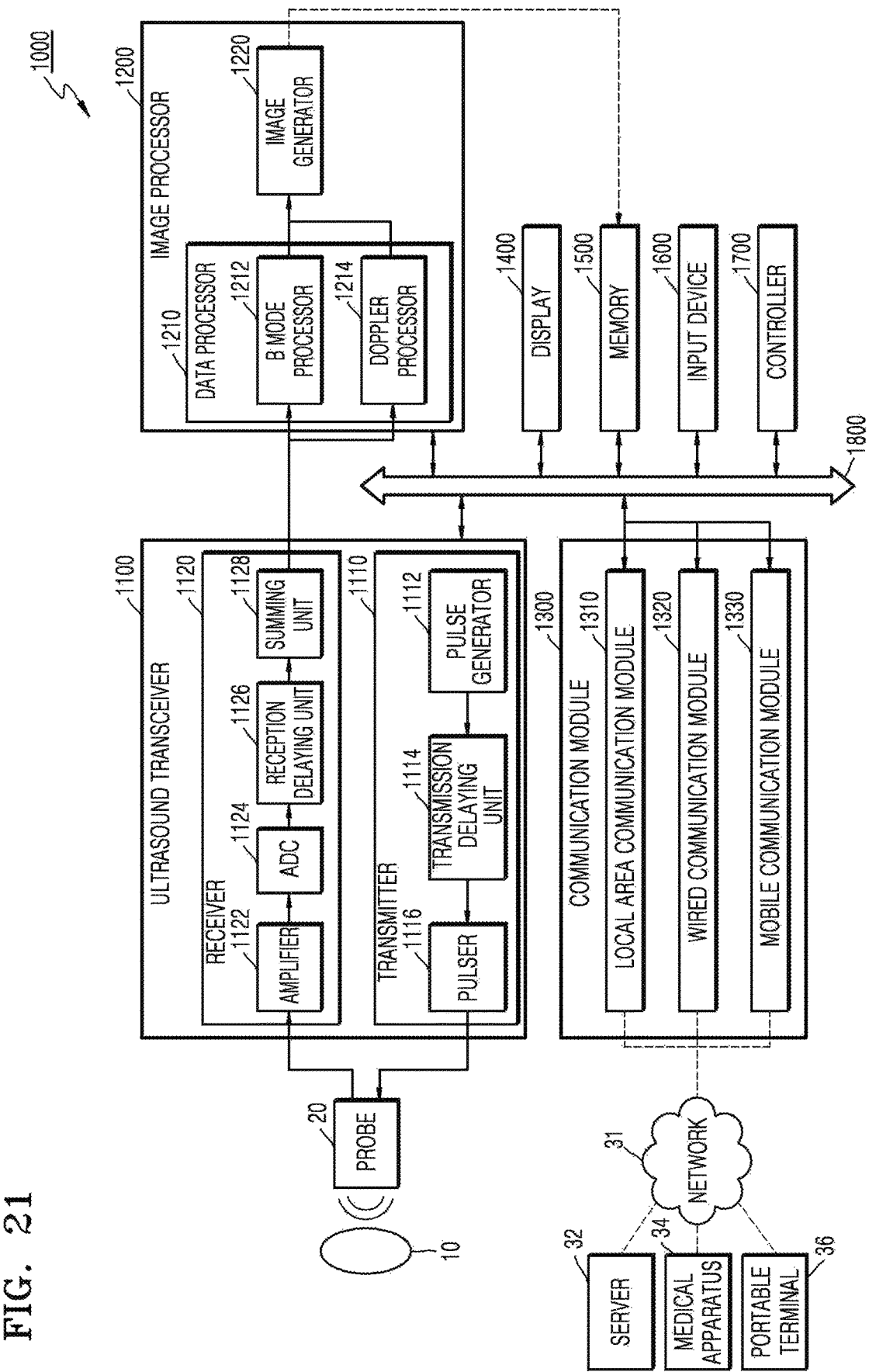
FIG. 21 is a block diagram of a structure of the ultrasound diagnosis apparatus, according to another exemplary embodiment.

FIG. 21 is a block diagram of a structure of the ultrasound diagnosis apparatus 1000, according to another exemplary embodiment.

The ultrasound diagnosis apparatus 1000 may include a probe 20, an ultrasound transceiver 1100, an image processor 1200, a communication module 1300, and a memory 1500 in addition to the processor 1700, the user input unit 1600, and the display 1400 shown in FIG. 20, and these components may be connected to one another via buses 1800.

The ultrasound diagnosis apparatus 1000 may be a cart type apparatus or a portable type apparatus. Examples of portable ultrasound diagnosis apparatuses may include, but are not limited to, a picture archiving and communication system (PACS) viewer, a smartphone, a laptop computer, a personal digital assistant (PDA), and a tablet PC.

The probe 20 transmits ultrasound waves to an object 10 in response to a driving signal applied by the ultrasound transceiver 1100 and receives echo signals reflected by the object 10. The probe 20 includes a plurality of transducers, and the plurality of transducers oscillate in response to electric signals and generate acoustic energy, that is, ultrasound waves. Furthermore, the probe 20 may be connected to the main body of the ultrasound diagnosis apparatus 1000 by wire or wirelessly, and according to embodiments, the ultrasound diagnosis apparatus 1000 may include a plurality of probes 20.

A transmitter 1110 supplies a driving signal to the probe 20. The transmitter 110 includes a pulse generator 1112, a transmission delaying unit 1114, and a pulser 1116. The pulse generator 1112 generates pulses for forming transmission ultrasound waves based on a predetermined pulse repetition frequency (PRF), and the transmission delaying unit 1114 delays the pulses by delay times necessary for determining transmission directionality. The pulses which have been delayed correspond to a plurality of piezoelectric vibrators included in the probe 20, respectively. The pulser 1116 applies a driving signal (or a driving pulse) to the probe 20 based on timing corresponding to each of the pulses which have been delayed.

A receiver 1120 generates ultrasound data by processing echo signals received from the probe 20. The receiver 120 may include an amplifier 1122, an analog-to-digital converter (ADC) 1124, a reception delaying unit 1126, and a summing unit 1128. The amplifier 1122 amplifies echo signals in each channel, and the ADC 1124 performs analog-to-digital conversion with respect to the amplified echo signals. The reception delaying unit 1126 delays digital echo signals output by the ADC 1124 by delay times necessary for determining reception directionality, and the summing unit 1128 generates ultrasound data by summing the echo signals processed by the reception delaying unit 1126. In some embodiments, the receiver 1120 may not include the amplifier 1122. In other words, if the sensitivity of the probe 20 or the capability of the ADC 1124 to process bits is enhanced, the amplifier 1122 may be omitted.

The image processor 1200 generates an ultrasound image by scan-converting ultrasound data generated by the ultrasound transceiver 1100. The ultrasound image may be not only a grayscale ultrasound image obtained by scanning an object in an amplitude (A) mode, a brightness (B) mode, and a motion (M) mode, but also a Doppler image showing a movement of an object via a Doppler effect. The Doppler image may be a blood flow Doppler image showing flow of blood (also referred to as a color Doppler image), a tissue Doppler image showing a movement of tissue, or a spectral Doppler image showing a moving speed of an object as a waveform.

A B mode processor 1212 extracts B mode components from ultrasound data and processes the B mode components. An image generator 1220 may generate an ultrasound image indicating signal intensities as brightness based on the extracted B mode components 1212.

Similarly, a Doppler processor 1214 may extract Doppler components from ultrasound data, and the image generator 1220 may generate a Doppler image indicating a movement of an object as colors or waveforms based on the extracted Doppler components.

According to an embodiment, the image generator 1220 may generate a three-dimensional (3D) ultrasound image via volume-rendering with respect to volume data and may also generate an elasticity image by imaging deformation of the object 10 due to pressure. Furthermore, the image generator 1220 may display various pieces of additional information in an ultrasound image by using text and graphics. In addition, the generated ultrasound image may be stored in the memory 1500.

A display 1400 displays the generated ultrasound image. The display 1400 may display not only an ultrasound image, but also various pieces of information processed by the ultrasound diagnosis apparatus 1000 on a screen image via a graphical user interface (GUI). In addition, the ultrasound diagnosis apparatus 1000 may include two or more displays 1400 according to embodiments.

The communication module 1300 is connected to a network 31 by wire or wirelessly to communicate with an external device or a server. The communication module 1300 may exchange data with a hospital server or another medical apparatus in a hospital, which is connected thereto via a PACS. Furthermore, the communication module 1300 may perform data communication according to the digital imaging and communications in medicine (DICOM) standard.

The communication module 1300 may transmit or receive data related to diagnosis of an object, e.g., an ultrasound image, ultrasound data, and Doppler data of the object, via the network 31 and may also transmit or receive medical images captured by another medical apparatus, e.g., a computed tomography (CT) apparatus, a magnetic resonance imaging (MRI) apparatus, or an X-ray apparatus. Furthermore, the communication module 1300 may receive information about a diagnosis history or medical treatment schedule of a patient from a server and utilizes the received information to diagnose the patient. Furthermore, the communication module 1300 may perform data communication not only with a server or a medical apparatus in a hospital, but also with a portable terminal of a medical doctor or patient.

The communication module 1300 is connected to the network 31 by wire or wirelessly to exchange data with a server 32, a medical apparatus 34, or a portable terminal 36. The communication module 1300 may include one or more components for communication with external devices. For example, the communication module 1300 may include a local area communication module 1310, a wired communication module 1320, and a mobile communication module 1330.

The local area communication module 1310 refers to a module for local area communication within a predetermined distance. Examples of local area communication techniques according to an embodiment may include, but are not limited to, wireless LAN, Wi-Fi, Bluetooth, ZigBee, Wi-Fi Direct (WFD), ultra wideband (UWB), infrared data association (IrDA), Bluetooth low energy (BLE), and near field communication (NFC).

The wired communication module 1320 refers to a module for communication using electric signals or optical signals. Examples of wired communication techniques according to an embodiment may include communication via a twisted pair cable, a coaxial cable, an optical fiber cable, and an Ethernet cable.

The mobile communication module 1330 transmits or receives wireless signals to or from at least one selected from a base station, an external terminal, and a server on a mobile communication network. The wireless signals may be voice call signals, video call signals, or various types of data for transmission and reception of text/multimedia messages.

The memory 1500 stores various data processed by the ultrasound diagnosis apparatus 1000. For example, the memory 1500 may store medical data related to diagnosis of an object, such as ultrasound data and an ultrasound image that are input or output, and may also store algorithms or programs which are to be executed in the ultrasound diagnosis apparatus 1000.

The memory 1500 may be any of various storage media, e.g., a flash memory, a hard disk drive, EEPROM, etc. Furthermore, the ultrasound diagnosis apparatus 1000 may utilize web storage or a cloud server that performs the storage function of the memory 1500 online.

The input device 1600 refers to a means via which a user inputs data for controlling the ultrasound diagnosis apparatus 1000. The input device 1600 may include hardware components, such as a keypad, a mouse, a touch pad, a touch screen, and a jog switch. However, embodiments of the present invention are not limited thereto, and the input device 1600 may further include any of various other input units including an electrocardiogram (ECG) measuring module, a respiration measuring module, a voice recognition sensor, a gesture recognition sensor, a fingerprint recognition sensor, an iris recognition sensor, a depth sensor, a distance sensor, etc.

The processor 1700 may control all operations of the ultrasound diagnosis apparatus 1000. In other words, the processor 1700 may control operations among the probe 20, the ultrasound transceiver 1100, the image processor 1200, the communication module 1300, the display 1400, the memory 1500, and the input device 1600 shown in FIG. 1.

All or some of the probe 20, the ultrasound transceiver 1100, the image processor 1200, the communication module 1300, the display 1400, the memory 1500, the input device 1600, and the processor 1700 may be implemented as software modules. However, embodiments of the present invention are not limited thereto, and some of the components stated above may be implemented as hardware modules. Also, at least one of the ultrasound transmission/reception unit 1100, the image processor 1200, and the communication module 1300 may be included in the control unit 1600; however, the inventive concept is not limited thereto.

The present invention can also be embodied as a storage medium including instruction codes executable by a computer such as a program module executed by the computer. A computer readable medium can be any usable medium which can be accessed by the computer and includes all volatile/non-volatile and removable/non-removable media. Further, the computer readable medium may include all computer storage and communication media. The computer storage medium includes all volatile/non-volatile and removable/non-removable media embodied by a certain method or technology for storing information such as computer readable instruction code, a data structure, a program module or other data. The communication medium typically includes the computer readable instruction code, the data structure, the program module, or other data of a modulated data signal such as a carrier wave, or other transmission mechanism, and includes any information transmission medium.

The terminology "unit" used herein may be a hardware component such as a processor or a circuit, and/or a software component that is executed by a hardware component such as a processor.

Although the embodiments of the present invention have been disclosed for illustrative purposes, one of ordinary skill in the art will appreciate that diverse variations and modifications are possible, without departing from the spirit and scope of the invention. Thus, the above embodiments should be understood not to be restrictive but to be illustrative, in all aspects. For example, respective elements described in an integrated form may be dividedly used, and the divided elements may be used in a state of being combined.

The exemplary embodiments should be considered in descriptive sense only and not for purposes of limitation. Descriptions of features or aspects within each embodiment should typically be considered as available for other similar features or aspects in other embodiments.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. An ultrasound diagnosis apparatus comprising:
a display configured to display a first cine frame selected by a user from among a plurality of cine frames, on a first area on a screen of the ultrasound diagnosis apparatus;
a user input unit configured to receive a user input of inputting additional information including a measurement value of a target within the first cine frame onto the first cine frame; and
a processor configured to:
in response to the user input of inputting the additional information which is represented on the first cine frame, generate a reference frame by representing the additional information on the first cine frame and automatically store the generated reference frame,
in response to the user input of inputting the additional information which is represented on the first cine frame, control the display to automatically display the generated reference frame on a second area on the screen,
control the display to display a user interface for selecting a type of the additional information, wherein the additional information is at least one of a measurement value of a distance, a width, a length, a volume, a ratio, and an angle, from among a plurality of types of the additional information, and
in response to a user input of selecting the type of the additional information which is at least one of the measurement values, control the display to preferentially display, on the second area, at least one reference frame in which the at least one of the measurement values of a target corresponding to the selected type is represented from among a plurality of reference frames.

2. The ultrasound diagnosis apparatus of claim 1, wherein the user input unit is configured to receive a user input of selecting the reference frame displayed on the second area, and
the display is configured to display the selected reference frame on the first area.

3. The ultrasound diagnosis apparatus of claim 1, wherein:
the user input unit is configured to receive a user input of selecting a second cine frame from among the plurality of cine frames by scrolling among the plurality of cine frames in an order of being captured, and a user input of selecting the reference frame displayed on the second area, and
in response to the user input of selecting the reference frame displayed on the second area, the processor is configured to change the selected cine frame from the second cine frame to the first cine frame corresponding to the selected reference frame.

4. The ultrasound diagnosis apparatus of claim 3, wherein the display is configured to display a marker representing a capturing order of the selected cine frame, and, as the first cine frame is determined as a cine frame selected via scrolling, the display is configured to change the displayed marker to a marker representing that the selected cine frame has changed from the second cine frame to the first cine frame, and configured to display the changed marker representing that the selected cine frame has changed from the second cine frame to the first cine frame.

5. The ultrasound diagnosis apparatus of claim 1, wherein:
the plurality of reference frames including the generated reference frame are displayed on the second area,
the processor is configured to receive a user input of rotating a knob included in the ultrasound diagnosis apparatus, and
in response to the user input of rotating the knob, the processor is configured to control the display so that the plurality of reference frames are sequentially selected.

6. The ultrasound diagnosis apparatus of claim 1, wherein:
the plurality of reference frames including the generated reference frame are displayed on the second area,
the user input unit is configured to receive the user input of selecting the type of the additional information, via the user interface.

7. The ultrasound diagnosis apparatus of claim 1, wherein the plurality of reference frames including the generated reference frame are displayed on the second area, and
in response to a user input of selecting the first cine frame, the processor is configured to control the display to preferentially display a reference frame captured at a time point close to the time point when the selected first cine frame is captured, from among the plurality of reference frames.

8. The ultrasound diagnosis apparatus of claim 1, wherein:
the user input unit is configured to receive a user input of re-selecting the first cine frame from among the plurality of cine frames by scrolling among the plurality of cine frames in an order of being captured, and
as the first cine frame is re-selected, the processor is configured to control the display to display, on the reference frame displayed on the second area, a marker representing that the reference frame displayed on the second area is a reference frame corresponding to the first cine frame.

9. The ultrasound diagnosis apparatus of claim 1, wherein the plurality of reference frames including the generated reference frame are displayed on the second area, and
in response to a user input of inputting the additional information onto the first cine frame, the processor is configured to control the display to preferentially display a reference frame to which a same type of additional information as a type of the input additional information has been input, from among the plurality of reference frames.

10. The ultrasound diagnosis apparatus of claim 1, wherein
the plurality of reference frames including the generated reference frame are displayed on the second area, the user input unit is configured to receive a user input of selecting at least one reference frame from among the plurality of reference frames, and
the processor controls the display to display the at least one reference frame as a group.

11. A method of displaying an ultrasound image, the method comprising:
displaying a first cine frame selected by a user from among a plurality of cine frames, on a first area on a screen of an ultrasound diagnosis apparatus;
receiving a user input of inputting additional information including a measurement value of a target within the first cine frame;
in response to the user input of inputting the additional information which is represented on the first cine frame, generating a reference frame by representing the additional information on the first cine frame and automatically storing the generated reference frame;
in response to the user input of inputting the additional information which is represented on the first cine frame, automatically displaying the generated reference frame on a second area on the screen;
displaying a user interface for selecting a type of the additional information, wherein the additional information is at least one of a measurement value of a distance, a width, a length, a volume, a ratio, and an angle, from among a plurality of types of the additional information; and
in response to a user input of selecting the type of the additional information which is at least one of the measurement values, displaying, on the second area, at least one reference frame in which the at least one of the measurement values of a target corresponding to the selected type is represented from among a plurality of reference frames.

12. The method of claim 11, further comprising:
receiving a user input of selecting the reference frame displayed on the second area; and
displaying the selected reference frame on the first area.

13. The method of claim 11, further comprising:
receiving a user input of selecting a second cine frame from among the plurality of cine frames by scrolling among the plurality of cine frames in an order of being captured;
receiving a user input of selecting the reference frame displayed on the second area; and
in response to the user input of selecting the reference frame displayed on the second area, changing the selected cine frame from the second cine frame to the first cine frame corresponding to the selected reference frame.

14. The method of claim 13, further comprising:
displaying a marker representing a capturing order of the selected cine frame; and
changing the displayed marker to a marker representing that the selected cine frame has changed from the second cine frame to the first cine frame.

15. The method of claim 11, wherein:
the plurality of reference frames including the generated reference frame are displayed on the second area, and
the method further comprises:
receiving a user input of rotating a knob included in the ultrasound diagnosis apparatus; and
in response to the user input of rotating the knob, sequentially selecting the plurality of reference frames.

16. The method of claim 11, wherein:

the plurality of reference frames including the generated reference frame are displayed on the second area, and the method further comprises receiving a user input of selecting the type of the additional information, via the user interface.

17. The method of claim 11, wherein:

the plurality of reference frames including the generated reference frame are displayed on the second area, and the method further comprises, in response to a user input of selecting the first cine frame, preferentially displaying a reference frame captured at a time point close to the time point when the selected first cine frame is captured, from among the plurality of reference frames.

18. The method of claim 11, further comprising:

receiving a user input of re-selecting the first cine frame from among the plurality of cine frames by scrolling among the plurality of cine frames in an order of being captured; and as the first cine frame is re-selected, displaying, on the reference frame displayed on the second area, a marker representing that the reference frame displayed on the second area is a reference frame corresponding to the first cine frame.

19. The method of claim 11, wherein:

the plurality of reference frames including the generated reference frame are displayed on the second area, and the method further comprises, in response to a user input of inputting additional information onto the first cine frame, preferentially displaying a reference frame to which a same type of additional information as a type of the input additional information has been input, from among the plurality of reference frames.

20. The method of claim 11, wherein:

the plurality of reference frames including the generated reference frame are displayed on the second area, and the method further comprises:

receiving a user input of selecting at least one reference frame from among the plurality of reference frames; and displaying the at least one reference frame as a group.

* * * * *